(12) United States Patent
Ueno et al.

(10) Patent No.: US 7,683,338 B2
(45) Date of Patent: Mar. 23, 2010

(54) RADIOLOGICAL IMAGING SYSTEM

(75) Inventors: Yuuichirou Ueno, Hitachi (JP); Hiroshi Kitaguchi, Naka (JP); Katsutoshi Tsuchiya, Hitachi (JP); Kensuke Amemiya, Hitachinaka (JP); Kazuma Yokoi, Hitachi (JP); Shinichi Kojima, Hitachi (JP); Norihito Yanagita, Hitachi (JP); Takafumi Ishitsu, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 383 days.

(21) Appl. No.: 10/874,359

(22) Filed: Jun. 24, 2004

(65) Prior Publication Data

US 2005/0067578 A1    Mar. 31, 2005

(30) Foreign Application Priority Data

Sep. 30, 2003    (JP)    ............... 2003-342437

(51) Int. Cl.
G01T 1/24    (2006.01)
(52) U.S. Cl. .................................. 250/370.09
(58) Field of Classification Search ............ 250/370.09, 250/370.08, 363.02, 363.03, 363.04; 378/4, 378/55, 63, 147; 600/425
See application file for complete search history.

(56) References Cited

U.S. PATENT DOCUMENTS

| | | | |
|---|---|---|---|
| 4,700,076 A | 10/1987 | Dorman et al. | |
| 4,794,257 A | 12/1988 | Baba et al. | |
| 4,868,393 A | 9/1989 | Kiri et al. | |
| 5,030,830 A | 7/1991 | Okada | |
| 5,316,831 A | 5/1994 | Nakajima et al. | |
| 5,537,452 A * | 7/1996 | Shepherd et al. | ............... 378/65 |
| 5,684,850 A * | 11/1997 | Warburton et al. | ............ 378/53 |
| 5,693,948 A | 12/1997 | Sayed et al. | |
| 5,742,060 A | 4/1998 | Ashburn | |
| 5,907,156 A | 5/1999 | Nishizawa et al. | |

(Continued)

FOREIGN PATENT DOCUMENTS

EP    0 734 076 A2    9/1996

(Continued)

OTHER PUBLICATIONS

Bergman, et al., "Technique to Obtain Positron Emission Mammography Images in Registration with X-ray Mammograms", Medical Physics, American Institute of Physics, vol. 25, No. 11, Nov. 1998, pp. 2119-2129.

(Continued)

*Primary Examiner*—David P Porta
*Assistant Examiner*—Faye Boosalis
(74) *Attorney, Agent, or Firm*—Dickstein Shapiro LLP

(57) ABSTRACT

The radiological imaging system which can improve an energy resolution and perform a diagnosis with high accuracy includes a bed for carrying an examinee H, first and second imaging apparatuses and disposed along the longitudinal direction of the bed. The first imaging apparatus has a plurality of semiconductor radiation detectors for detecting γ-rays emitted from the examinee H, arranged around the bed, the second imaging apparatus has an X-ray source for emitting X-rays to the examinee H and a radiation detector for detecting X-rays which have been emitted from the X-ray source and passed through the examinee H, and the bed is shared by the first imaging apparatus and the second imaging apparatus.

24 Claims, 20 Drawing Sheets

U.S. PATENT DOCUMENTS

| | | | |
|---|---|---|---|
| 6,173,031 B1 * | 1/2001 | Hoffman et al. | 378/19 |
| 6,205,347 B1 * | 3/2001 | Morgan et al. | 600/407 |
| 6,236,051 B1 * | 5/2001 | Yamakawa et al. | 250/370.1 |
| 6,346,706 B1 | 2/2002 | Rogers et al. | |
| 6,403,964 B1 | 6/2002 | Kyyhkynen | |
| 6,448,559 B1 * | 9/2002 | Saoudi et al. | 250/367 |
| 6,490,476 B1 * | 12/2002 | Townsend et al. | 600/427 |
| 6,541,773 B1 | 4/2003 | Iwabuchi et al. | |
| 6,583,420 B1 | 6/2003 | Nelson et al. | |
| 6,590,215 B2 * | 7/2003 | Nygard et al. | 250/370.09 |
| 6,591,127 B1 * | 7/2003 | McKinnon | 600/411 |
| 6,621,084 B1 | 9/2003 | Wainer et al. | |
| 6,631,284 B2 * | 10/2003 | Nutt et al. | 600/427 |
| 6,658,082 B2 * | 12/2003 | Okumura et al. | 378/19 |
| 6,661,866 B1 * | 12/2003 | Limkeman et al. | 378/19 |
| 6,703,617 B1 | 3/2004 | Spartiotis et al. | |
| 6,810,103 B1 * | 10/2004 | Tybinkowski et al. | 378/20 |
| 6,841,782 B1 * | 1/2005 | Balan et al. | 250/363.02 |
| 2002/0064252 A1 | 5/2002 | Igarashi et al. | |
| 2002/0090050 A1 | 7/2002 | Nutt et al. | |
| 2003/0004405 A1 | 1/2003 | Townsend et al. | |
| 2003/0030721 A1 | 2/2003 | Nyholm | |
| 2003/0078489 A1 | 4/2003 | DeSilets et al. | |
| 2003/0128801 A1 * | 7/2003 | Eisenberg et al. | 378/19 |
| 2003/0179853 A1 * | 9/2003 | Amemiya et al. | 378/63 |
| 2005/0067572 A1 | 3/2005 | Amemiya | |
| 2005/0067573 A1 | 3/2005 | Albert et al. | |
| 2008/0277589 A1 * | 11/2008 | Seino et al. | 250/370.13 |

FOREIGN PATENT DOCUMENTS

| | | |
|---|---|---|
| EP | 1 271 181 A2 | 1/2003 |
| EP | 1 325706 | 7/2003 |
| JP | 60086481 | 5/1985 |
| JP | 63-049140 | 3/1988 |
| JP | 63049140 | 3/1988 |
| JP | 4-10384 | 1/1992 |
| JP | 5-333157 | 12/1993 |
| JP | 7-20245 | 1/1995 |
| JP | 7020245 | 1/1995 |
| JP | 7-29489 | 6/1995 |
| JP | 9-275223 | 10/1997 |
| JP | 9-281241 | 10/1997 |
| JP | 11-344573 | 12/1999 |
| JP | 11344573 | 12/1999 |
| JP | 2000-131440 | 5/2000 |
| JP | 2003-79614 | 3/2003 |
| JP | 2003 90882 | 3/2003 |
| JP | 2003-116835 | 4/2003 |
| JP | 2003-167058 | 6/2003 |
| JP | 2003-232855 | 8/2003 |
| WO | WO 86/07531 | 12/1986 |

OTHER PUBLICATIONS

Japanese Office Action for Application No. 2006-264038.
Japanese Office Action for Application No. 2004-199470.

* cited by examiner

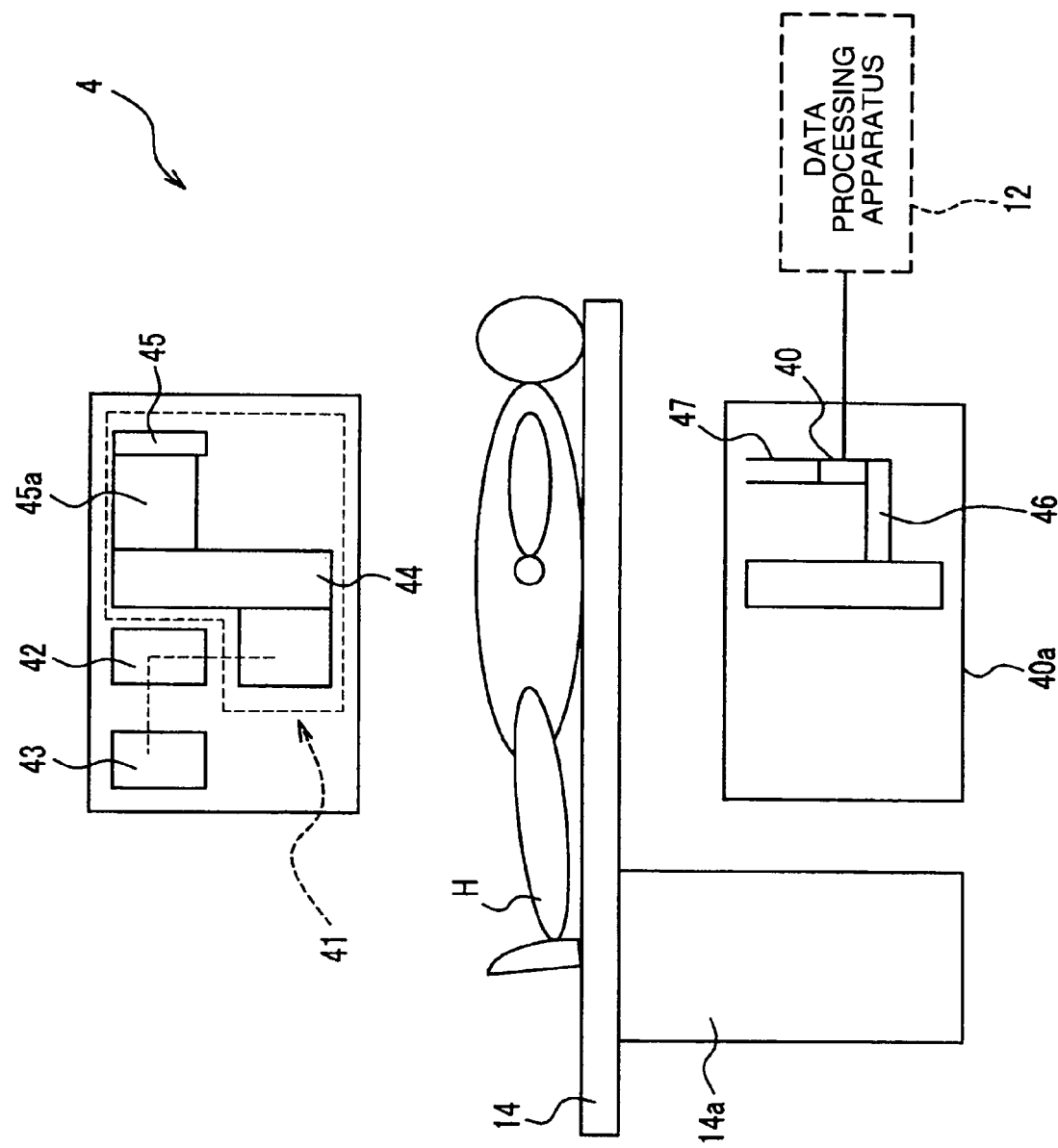

FIG. 17

EXAMINATION TYPE   PET AND CT ● ONLY PET ○ ONLY CT ○

TIME FROM START TO END OF EXAMINATION   [30 ◁▷] MINUTES

IMAGING AREA (CONCERNED AREA)   START POSITION [*** ▷]   END POSITION [*** ▷]

NUMBER OF SLICES [ ◁▷]   SLICING INTERVALS [ ◁▷]

TIMING OF CT SCAN   [***** ▷]

TUBE VOLTAGE [* ◁▷] kV   TUBE CURRENT [* ◁▷] mA   ABSORBED DOSE [*** ◁▷] mGy

...   ...   ...

[DISPLAY]

CLICK "DISPLAY" BUTTON TO CREATE AND DISPLAY EXAMINATION SEQUENCE

[START EXAMINATION]

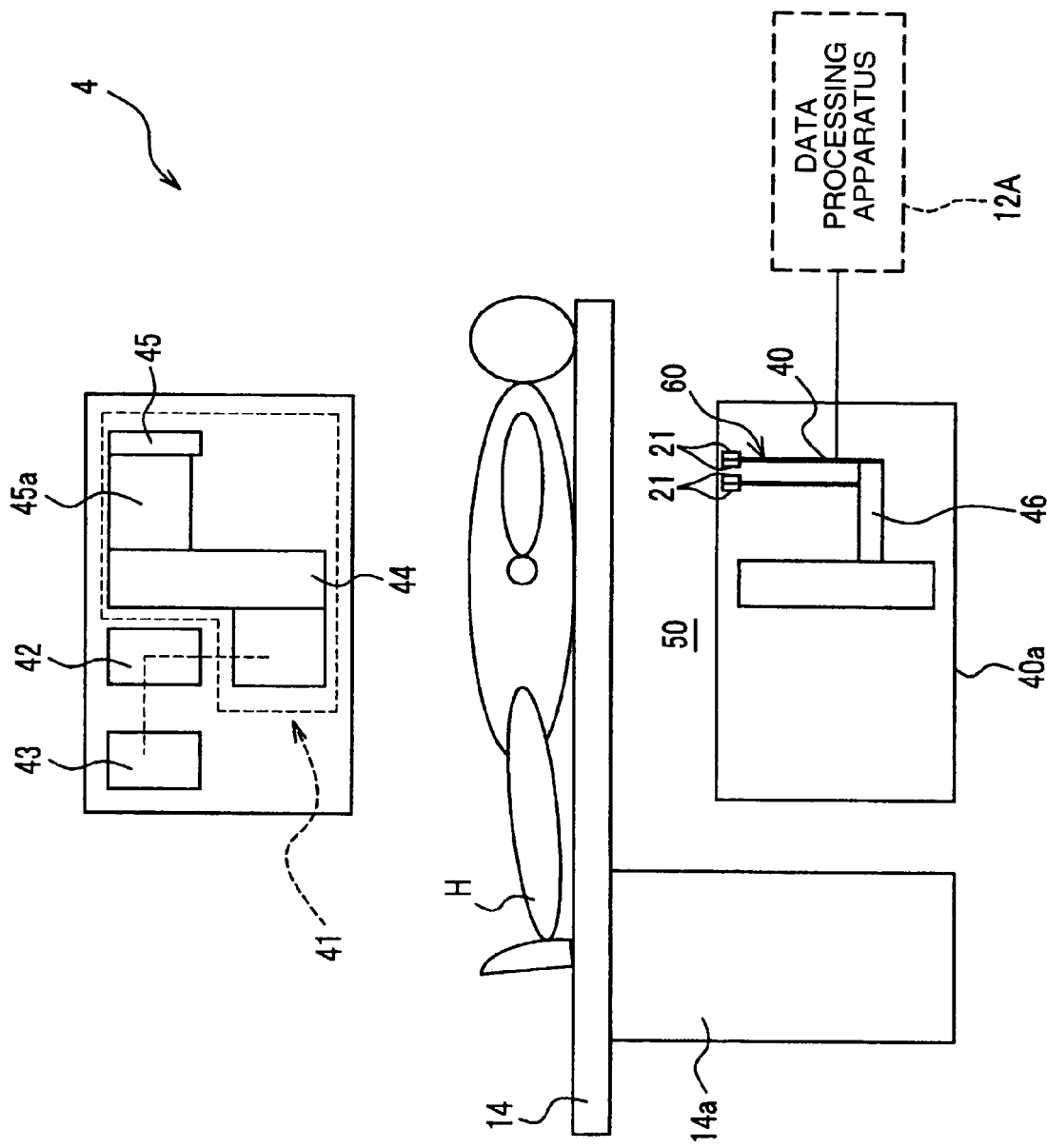

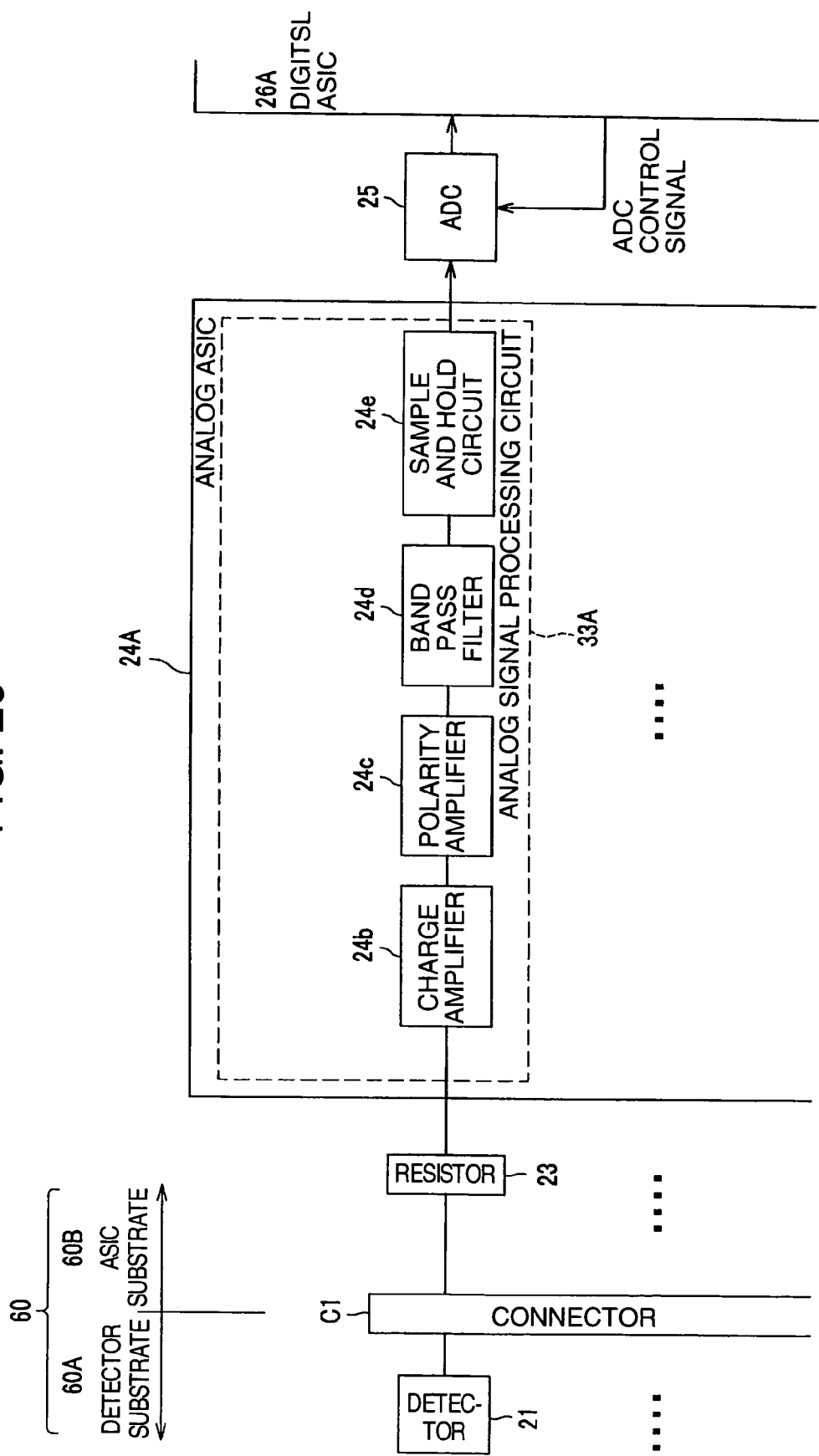

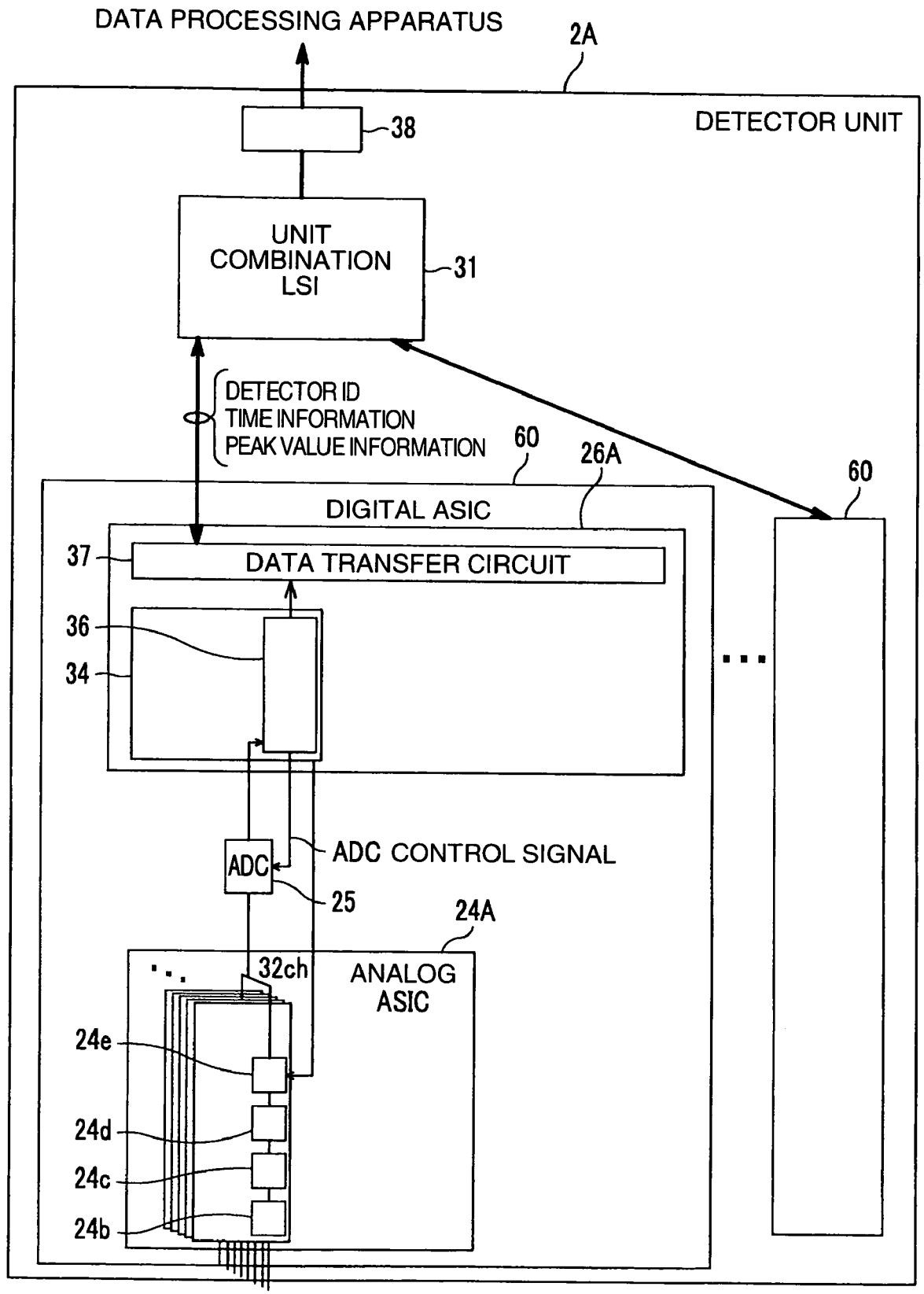

RADIOLOGICAL IMAGING SYSTEM

CROSS-REFERENCE TO RELATED APPLICATION

The present application is related to a U.S. Ser. No. 10/874,343 being filed based on Japanese Patent Application No. 2003-340688 filed on Sep. 30, 2003, the entire content of which is incorporated herein by reference.

BACKGROUND OF THE INVENTION

The present invention relates to a radiological imaging system using a radiation and particularly relates to a radiological imaging system suitable for carrying out two or more kinds of radiological examinations including an X-ray CT examination and a positron emission computed tomography (hereinafter referred to as "PET") examination.

Examination techniques using radiations realize nondestructive examinations in the body of an examinee. Particularly radiological examination techniques for a human body include X-ray CT, PET, single photon emission computed tomography (hereinafter referred to as "SPECT").

In all of these techniques, a physical quantity to be examined is measured as an integral value of the flying direction of a radiation and the integral value is inversely projected, so that a physical quantity of each voxel in the body of an examinee is calculated and an image is created. In these techniques, it is necessary to process an enormous amount of data and extremely fine images can be provided at high speed due to the rapid development of computer technology in recent years.

The X-ray CT technique measures the intensity of X-rays having passed through an examinee and images the morphological information of the examinee according to a rate of X-rays passing through the body. X-rays are radiated from an X-ray source to the examinee, the intensity of X-rays having passed through the body is measured by a detection element disposed on the other side of the examinee, and the distribution of integrated absorption coefficients of the examinee is measured. Based on the integrated absorption coefficients, an absorption coefficient of each voxel is determined using filtered back projection method described in IEEE Transactions on Nuclear Science, NS-21 vol., page 21, and the value is converted into a CT value. A source of about 80 keV is frequently used for X-ray CT.

Meanwhile, PET and SPECT are methods capable of detecting a function and metabolism at a molecular biological level where detection cannot be performed by X-ray CT, thereby providing a functional image of a body. In PET, radioactive chemicals labeled positron emitting nuclides such as $^{18}$F, $^{15}$O, and $^{11}$C are administered, and the distribution is measured and imaged. The chemicals include fluorodeoxyglucose (2-[F-18]fluoro-2-deoxy-D-glucose, $^{18}$FDG), which highly accumulates on a tumor tissue according to glucose metabolism and is used to identify a tumor region.

A radionuclide taken in the body decays and emits a positron (β+). The emitted positron releases a pair of annihilated γ-rays having an energy of 511 keV when being bound with electrons and annihilated. Since the pair of annihilated γ-rays are radiated substantially in opposite directions (180°±0.6°), the pair of annihilated γ-rays are simultaneously detected by detector elements which are arranged so as to surround the examinee, and radiating direction data is accumulated to obtain projection data. By inversely projecting the projection data (using the filtered back projection method), the emitting position (position where the radionuclide accumulates) can be identified and imaged.

In SPECT, radioactive chemicals labeled single photon emitting nuclides are administered and the distribution is measured and imaged. A single γ-ray with an energy of about 100 keV is radiated from the chemicals, and the single γ-ray is measured by the detection element. Since the flying direction cannot be identified in the measurement of the single γ-ray, a collimator is inserted at the front of the detection element and only γ-rays in a specific direction are detected, so that projection data is obtained in SPECT. As in the case of PET, projection data is inversely projected by using the filtered back projection method, etc., so that image data is obtained. SPECT is different from PET in that coincidence detection is not necessary due to single γ-ray measurement and the number of detection elements is small. Thus, the configuration of the apparatus is simple with relatively low cost. On the other hand, since SPECT uses a collimator, the detection rate of γ-rays is low and picture quality is poor in ordinary cases.

As described above, in PET and SPECT, a functional image is obtained using body metabolism. Thus, although a part where chemicals accumulate can be extracted with high contrast, the positional relationship of surrounding organs cannot be understood. For this reason, attention is being given to techniques for combining a morphological image of X-ray CT and a functional image of PET and SPECT to conduct a higher level of diagnosis (refer to JP-A-7-20245 (paragraph No. 0010, FIG. 1)).

In a radiological imaging system where a morphological image of conventional X-ray CT and a functional image of PET and SPECT are combined, a scintillator is used as a γ-ray detector to obtain a functional image of PET, SPECT and so on. The scintillator temporarily transforms a received γ-ray into visible light and then transforms the light into an electric signal by using a photomultiplier tube (photomultiplier). The scintillator has a low resolution of energy because the number of generated photons is small in the transformation into visible light and the two steps of transformation are necessary as described above. Thus, it is not always possible to conduct an accurate diagnosis. Particularly a quantitative evaluation cannot be made in 3D imaging of PET due to a reduction in energy resolution. This is because a γ-ray energy threshold value has to be reduced due to a low energy resolution and internal scattering, which is noise increased in 3D imaging, is frequently detected. Therefore, a PET apparatus of a scintillator system generally comprises a 2D imaging function to conduct a highly quantitative examination. In the 2D imaging, septa are inserted in the scintillator to prevent the entry of γ-rays from a part other than a 2D region.

Further, absorption correction is necessary to obtain an image with higher accuracy in a PET examination. γ-rays from a deep portion of the body are prone to be absorbed in the body as compared with a body surface. High picture quality and high quantitativeness can be achieved by correcting an amount of absorbed γ-rays in the body (absorption correction). In a PET apparatus of a single gantry system, when absorption correction is performed, it is necessary to hold a source and carry out measurement while rotating the source in the scintillator.

Therefore, in the PET apparatus of the scintillator system, the gantry has a large size due to the photomultiplier, septa, and the source for absorption correction. Moreover, in the case of a radiological imaging system having a conventional serial arrangement of X-ray CT, PET, SPECT, etc., the overall apparatus is prone to increase in size, thereby intimidating an examinee. Such a problem has to be solved.

An object of the present invention is to provide a radiological imaging system which can improve an energy resolution and achieve an accurate diagnosis.

SUMMARY OF THE INVENTION

In order to solve the problem, in a first invention, semiconductor radiation detectors are used for a first imaging apparatus (PET imaging apparatus) to increase detection accuracy. In this configuration, the semiconductor radiation detectors are used to directly detect a radiation, thereby improving a position resolution and an energy resolution. Further, since an energy resolution can be improved, internal scattering is removed (noise is reduced). Therefore, it is possible to improve quantitativeness in 3D imaging and eliminate the need for the septa for 2D imaging, thereby miniaturizing the apparatus. Further, detection elements can be smaller in size, achieving a radiological imaging system which is entirely miniaturized.

Besides, since absorption correction can be performed using a second imaging apparatus (X-ray CT imaging apparatus), it is not necessary to provide an absorption correction source (γ-ray, etc.) in the first imaging apparatus, thereby further miniaturizing the apparatus.

In a second invention, a semiconductor radiation detector is used as a radiation detector of the second imaging apparatus (X-ray CT imaging apparatus). In this configuration, the detection elements can be smaller in size, achieving a radiological imaging system which is entirely miniaturized.

In a third invention, the first imaging apparatus (PET imaging apparatus) is formed with a smaller size than the second imaging apparatus (X-ray CT imaging apparatus), and the first imaging apparatus is disposed in front of the second imaging apparatus. Thus, the overall apparatus becomes less intimidating to an examinee.

The present invention makes it possible to improve an energy resolution and achieve an accurate diagnosis.

Other objects, features and advantages of the invention will become apparent from the following description of the embodiments of the invention taken in conjunction with the accompanying drawings.

BRIEF DESCRIPTION OF THE DRAWINGS

FIG. 14 is a diagram schematically showing an X-ray CT imaging apparatus;

FIG. 17 is a diagram showing an example of an operation screen displayed on a display apparatus;

FIG. 18 is a diagram schematically showing the configuration of the X-ray CT imaging apparatus serving as a radiation examination apparatus according to another embodiment;

FIG. 20 is a block diagram schematically showing an analog detection circuit;

FIG. 21 is a block diagram which schematically shows the configuration of a digital ASIC and the connection relationship between an analog ASIC and the digital ASIC.

DESCRIPTION OF THE EMBODIMENTS

The following will specifically describe a radiological imaging system according to a preferred embodiment of the present invention with reference to the accompanying drawings. The following will discuss a PET imaging apparatus which is a first imaging apparatus constituting the radiological imaging system of the present embodiment, an X-ray CT imaging apparatus which is a second imaging apparatus, and elements such as a semiconductor radiation detector applied to the present embodiment.

Embodiment 1

Figure 1:
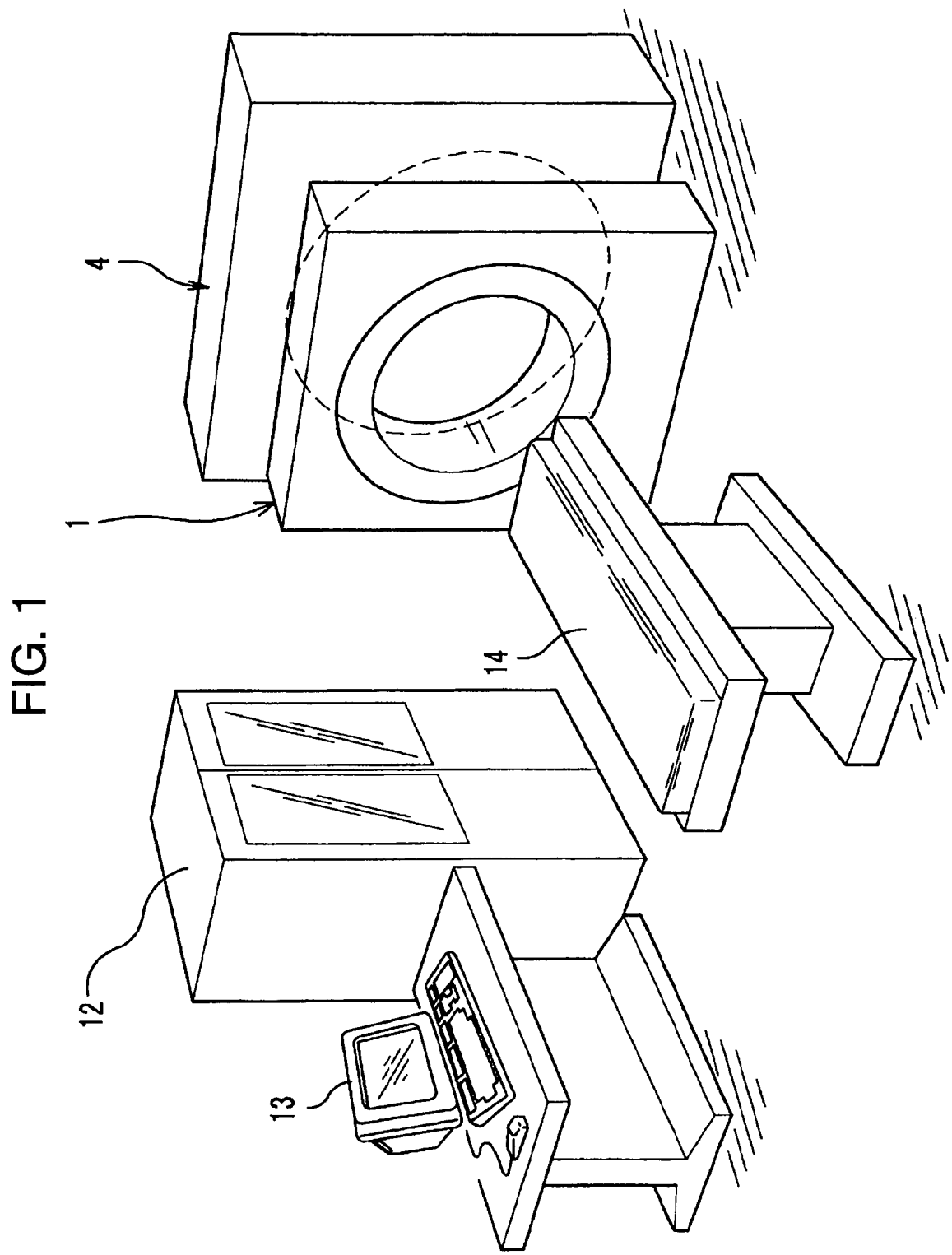
FIG. 1 is a perspective view showing the configuration of a radiological imaging system according to the present embodiment.
Figure 2:
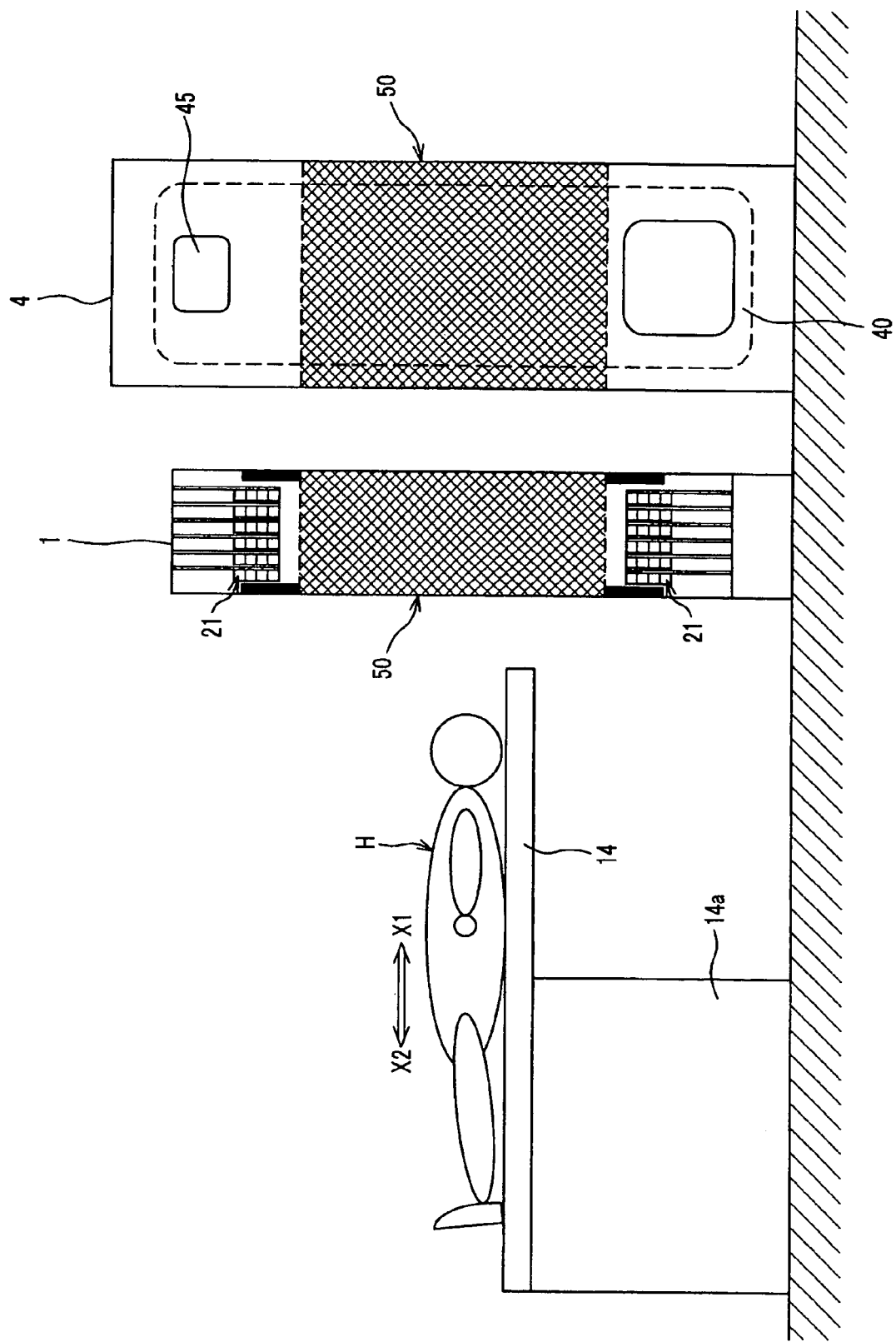
FIG. 2 is a diagram schematically showing a PET imaging apparatus and an X-ray CT imaging apparatus of FIG. 1.

As shown in FIGS. 1 and 2, the radiological imaging system of the present embodiment has two independent gantries which comprise a bed 14 serving as a berthing apparatus, a PET imaging apparatus 1 serving as a first imaging apparatus, and an X-ray CT imaging apparatus 4 serving as a second imaging apparatus. As shown in FIG. 1, the radiological imaging system includes a data processing apparatus 12 and a display apparatus 13. An examinee (subject) H is loaded on the bed 14 which can move forward and backward along the body axis direction (X1 and X2 directions) of the examinee H, and the examinee H is imaged by the PET imaging apparatus 1 and the X-ray CT imaging apparatus 4.

A. (PET Imaging Apparatus)

The PET imaging apparatus 1 includes a number of semiconductor radiation detectors 21 (FIGS. 4, 8, 11). γ-rays radiated from the inside of the examinee H are detected by the semiconductor radiation detectors (hereinafter, simply referred to as detectors) 21. The PET imaging apparatus 1 has an integrated circuit (ASIC) for measuring a peak value of the γ-ray and detection time, so that the peak value and detection time of the detected radiation (γ-ray) are measured.

Figure 3:
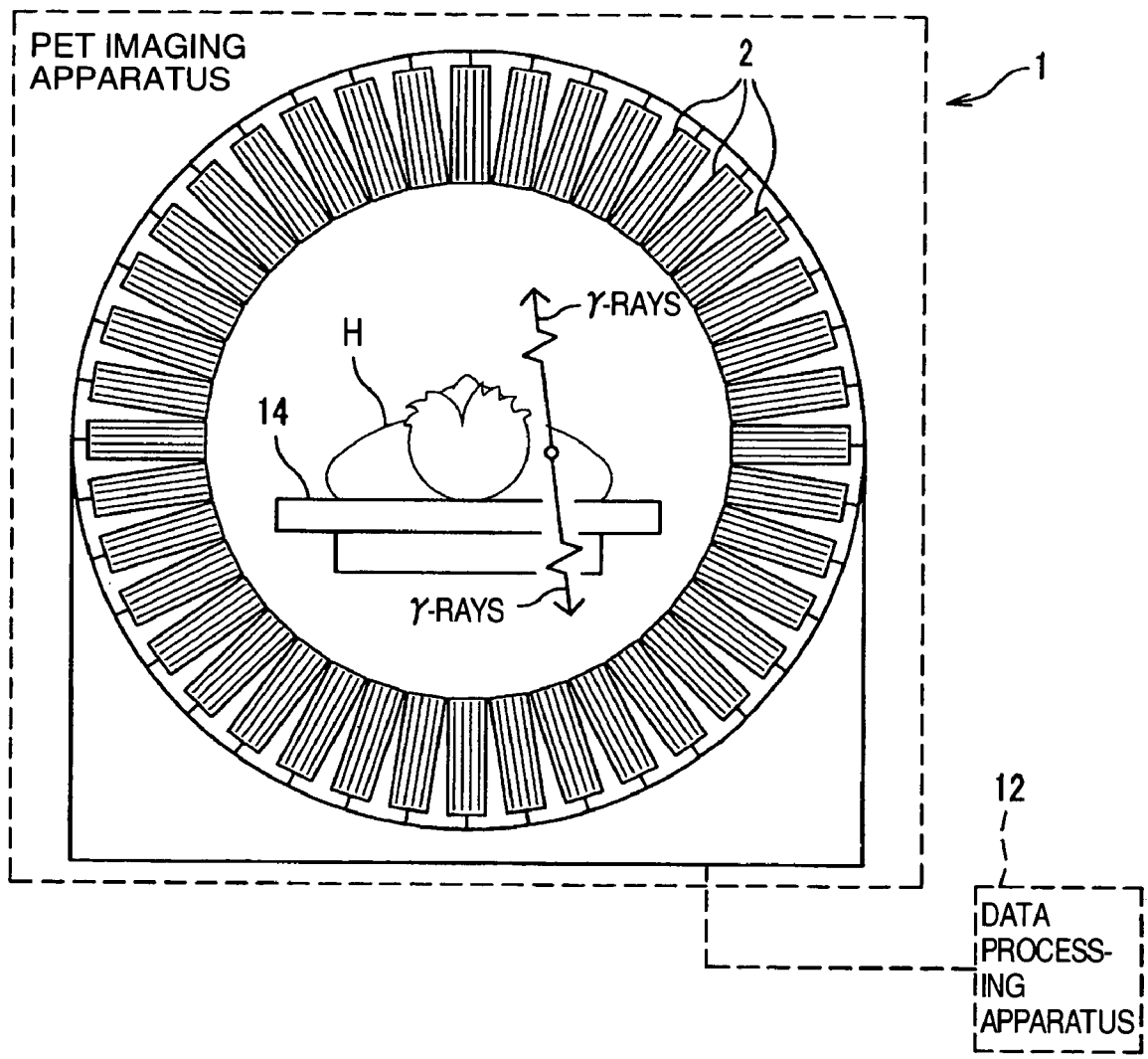
FIG. 3 schematically shows a sectional view along the circumferential direction of the PET imaging apparatus shown in FIG. 1.

As shown in FIG. 3, in the PET imaging apparatus 1, a number of detector units 2 (specifically shown in FIG. 11) are arranged like a circle to detect a γ-ray radiated from the examinee H. The detector unit 2 stores a plurality of combined substrates 20 (specifically shown in FIGS. 8A and 8B) each of which has a number of detectors 21. The examinee H serving as a subject lies on the bed 14 so as to be positioned at the center of the PET imaging apparatus 1. At this point, the detectors 21 surround the bed 14. From the detector units 2, γ-ray peak value information and γ-ray detection time information that are obtained based on a detection signal when the detectors 21 interact with γ-rays, and the address information (detector ID) of the detector 21 are outputted for each of the detectors 21 included in the detector unit 2. The configurations of the detector 21, the combined substrate 20, and the detector unit 2 will be specifically described later.

Incidentally, radioactive chemicals, e.g., fluorodeoxyglucose (FDG) containing $^{18}F$ having a half-life of 110 minutes are administered to the examinee H. From the body of the examinee H, γ-rays (annihilated γ-rays) are radiated when positrons emitted from the FDG are annihilated.

As shown in FIG. 1, the PET imaging apparatus 1 is formed with a smaller housing than that of the X-ray CT imaging apparatus 4, which will be described later, and the PET imaging apparatus 1 is disposed in front of the X-ray CT imaging apparatus 4 in the body axis direction (directions of X1 and X2 arrows in FIG. 1) of the examinee H.

The detail of the PET imaging apparatus 1 will be described below.

(Semiconductor Radiation Detector)

Figure 4:
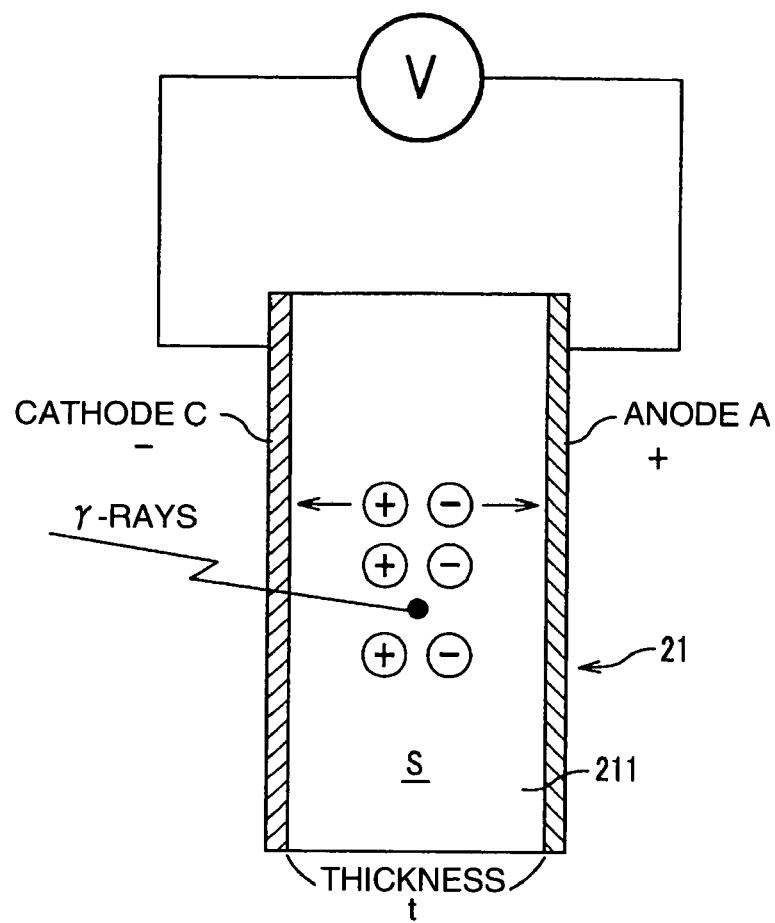
FIG. 4 is a diagram schematically showing the structure of the minimum configuration of a semiconductor radiation detector.

First, the detector 21 applied to the present embodiment will be described below. As shown in FIG. 4, the detector 21 is configured (minimum configuration) so that both sides of a semiconductor radiation sensor (hereinafter, referred to as a sensor) 211 composed of a plate-like semiconductor material S are covered with electrodes (anode A, cathode C) shaped like thin plates (films). In this configuration, the semiconductor material S is composed of any one of single crystals including CdTe (cadmium telluride), TlBr (thallium bromide), and GaAs (gallium arsenide). Further, the electrodes (anode A, cathode C) are made of any one of materials including Pt (platinum), Au (gold), and In (indium). In the following explanation, the semiconductor material S composed of a single crystal of CdTe is sliced. Moreover, a detecting radiation is a γ-ray of 511 KeV that is used in the PET imaging apparatus 1.

Referring to FIG. 4, the detection principle of a γ-ray in the detector 21 will be schematically described below. When a γ-ray is incident on the detector 21 and the γ-ray and the semiconductor material S constituting the detector 21 interact with each other, holes and electrons (schematically indicated as "+" and "−" in FIG. 4) are generated in pairs up to an amount in proportion to the energy of the γ-ray. In this configuration, voltage for collecting charge is applied across the electrodes of the anode A and the cathode C of the detector 21 (e.g., 300V). Thus, the holes are attracted to the cathode C and the electrons are attracted to the anode A. According to a comparison between the holes and the electrons, the electrons have relatively higher mobility and thus the electrons reach the anode in a relatively short time. On the other hand, the holes have relatively low mobility and thus the holes reach the cathode in a relatively long time. Incidentally, the holes may disappear before reaching the electrode.

Figure 5:
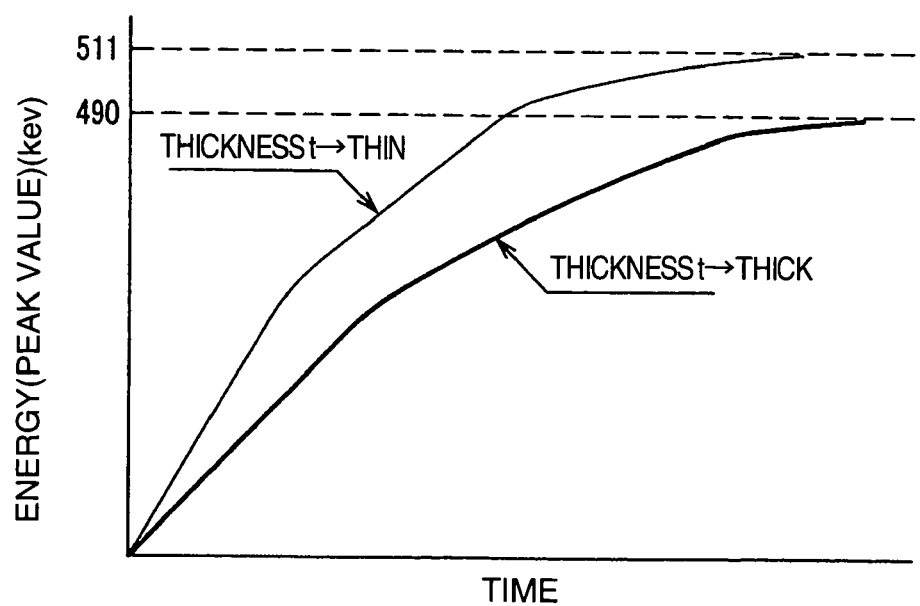
FIG. 5 is a graph for comparing "time-peak value curves" of a large thickness t and a small thickness t for the semiconductor material of the semiconductor radiation detector.

As shown in FIG. 5 in which the "time–peak value curves" are compared with each other regarding a large thickness and a small thickness of the semiconductor material S of the detector 21 (sensor 211), the semiconductor material S with the smaller thickness t rises in peak value more quickly and has a higher peak value. A quickly rising peak value contributes to, for example, higher accuracy of coincidence detection in the PET. Further, a high peak value contributes to a higher energy resolution. In this way, the smaller thickness t increases a peak value more quickly and achieves a higher peak value (higher efficiency of collecting charge). This is because the electrons and holes reach the electrodes (anode A, cathode C) in a short time (time of collecting charge). Another reason is that the holes which may disappear on their way can reach the electrode (cathode C) due to a short distance without disappearance. Incidentally, the thickness t can be also expressed as a distance between the electrodes of the anode A and the cathode C which face each other.

The sensor 211 preferably has a thickness (distance between the electrodes) t of 0.2 to 2 mm. When the thickness t is 2 mm or larger, a peak value rises slowly and becomes lower. Meanwhile, when the thickness t is 0.2 mm or smaller, the thicknesses (volumes) of the electrodes (anode, cathode) relatively increase. In the case of installation on a substrate, the important semiconductor material S to interact with a radiation decreases in ratio. That is, when the thickness t of the semiconductor material S is reduced, the electrode not interacting with a γ-ray relatively increases in thickness and meanwhile the semiconductor material S interacting with the γ-ray relatively decreases in ratio, resulting in lower sensitivity for detecting the γ-ray (the γ-ray passes by the sensor) Further, when the thickness t is small, a number of leak currents occur and do not permit the application of high voltage for collecting charge.

For the same reason, it is more preferably that the semiconductor material S has a thickness t of 0.5 to 1.5 mm. The preferable thickness t more positively enables detection of a γ-ray and a more accurate measurement of a peak value.

Since the PET imaging apparatus 1 conducts a coincidence detection, it is necessary to accurately measure the time of detection of a γ-ray. For example, in FIG. 4, the detection time is changed depending upon whether the interaction position of the γ-ray and the semiconductor material S is closer to the cathode C or the anode A. That is, since the holes move at low speed, an interaction occurring closer to the anode A causes relatively late detection. An interaction occurring closer to the cathode C causes relatively early detection (closer to real time). That is, even when a γ-ray interacts with semiconductor material S in the same sensor 211, the detection time is changed by the interaction position. To be specific, a large thickness t causes a large difference of the detection time depending upon the interaction position. Although such a phenomenon is not a serious problem in other fields, the PET imaging apparatus 1 for conducting a coincidence detection on the order of nsec (nanosecond) has a serious problem. Therefore, in this sense, the detection time can be properly determined in the range of thicknesses as described above. The detection time of the PET imaging apparatus 1 is determined by LET method and CFD method.

Figure 6:
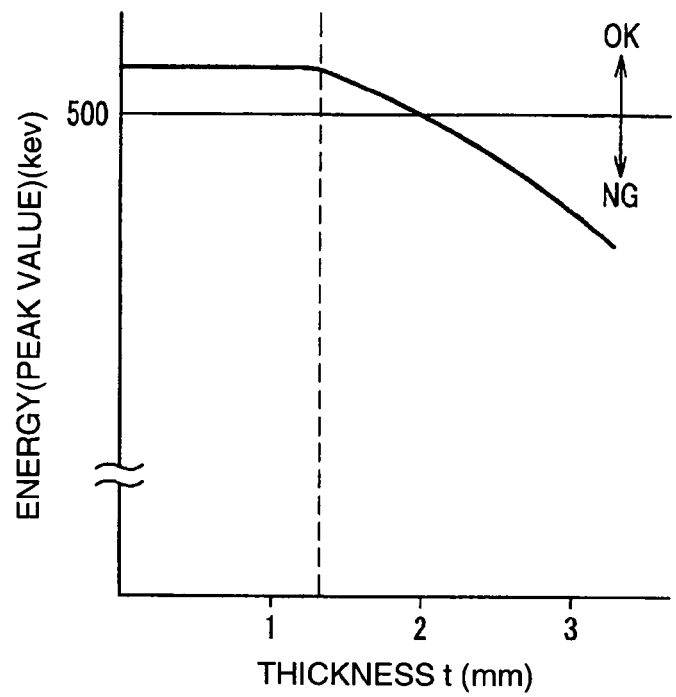
FIG. 6 is a graph schematically showing the relationship of a thickness t of the semiconductor material of the semiconductor radiation detector and a peak value (maximum value)

As shown in FIG. 6 schematically illustrating the relationship between a peak value (maximum value) and a thickness t of the semiconductor material S of the detector 21, the larger the thickness t of the semiconductor material S, the smaller the peak value. The reason why the peak value decreases is, for example, is that the holes disappear before reaching the electrodes. When the thickness t is 2 mm or larger, the peak value of a detected radiation becomes smaller than a threshold value for discriminating a γ-ray of 511 KeV. Thus, as described above, it is not preferable to increase the thickness t of the semiconductor material S to more than 2 mm.

Figure 7:
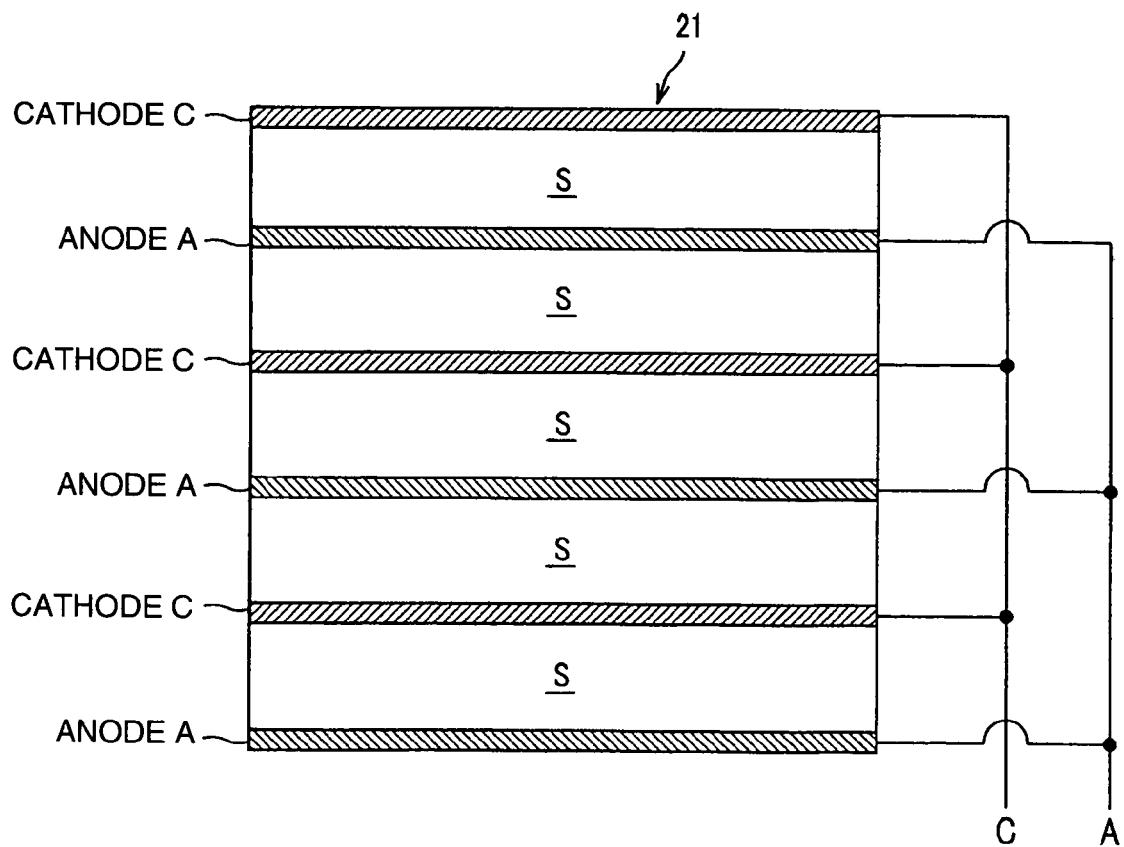
FIG. 7 is a diagram schematically showing the configuration of the semiconductor radiation detector having a laminated structure of the semiconductor material and electrodes (anode, cathode)

As shown in FIG. 7, the detector 21 has the semiconductor material S laminated into five layers each of which is disposed between the cathode C and the anode A (sensor 211). The detector 21 is a single-layer detector in which each layer of the semiconductor material S has the above-described thickness t (0.2 to 2 mm (more preferably 0.5 to 1.5 mm)). The anode A and the cathode C are about 20 μm in thickness. Incidentally, in the detector 21 having the laminated structure of FIG. 7, since the anodes A are connected to one another and the cathodes C are connected to one another, each layer does not detect a radiation separately from the other layers. In other words, when a γ-ray and the semiconductor material S interact with each other, it is not decided whether the interaction occurs in the top layer or the bottom layer. As a matter of course, detection may be carried out in each layer. Incidentally, the five-layer structure is constructed for the following reason: When the thickness t of the semiconductor material S is small, a peak value increases quickly to a higher value but more γ-rays pass through the material in the smaller thickness t, whereas the five-layer structure can reduce the number of γ-rays passing through the material to increase interactions between the semiconductor material S and the γ-rays (to increase the number of counts) while increasing the efficiency of collecting charge.

With the detector 21 having the laminated structure, it is possible to obtain a more preferable increase rate (rise) in peak value and a more accurate peak value, and increase the number of γ-rays (the number of counts) interacting with the semiconductor material S (increase sensitivity).

The detector 21 does not always have to have such a laminated structure. A single-layer structure is also applicable and two to four layers may be provided for a properly layered structure.

The electrodes (anode A, cathode C) preferably have an area s of 4 to 120 square millimeters. An increase in the area s increases a capacitance (stray capacitance) of the detector 21. Noise is more likely to be superimposed due to the increased stray capacitance. Thus, it is preferable to minimize the electrode area s. Further, charge generated during the detection of γ-rays is partly accumulated in the stray capacitance and thus the increased stray capacitance reduces charge accumulated in a charge-sensitive amplifier 24b of an analog ASIC 24 (FIG. 9) and reduces an output voltage (peak value). When CdTe is used as the detector 21, the detector 21 has a relative dielectric constant of 11. When the detector 21 has the area s of 120 square millimeters and the thickness t of 1 mm, the capacitance is 12 pF which is not negligible in consideration of a connectors and the like having a stray capacitance of several pF in a circuit. Therefore, it is preferable that the electrode area s is 120 square millimeters or smaller.

Further, the lower limit value of the electrode area s is determined by the position resolution of the PET imaging apparatus 1. The position resolution of the PET imaging apparatus 1 is determined by the range of positrons and so on in addition to the size (array pitch) of the detector 21. Since a positron of $^{18}F$ has a range of 2 mm, it is useless to set the size of the detector 21 at 2 mm or smaller. A packaging method for minimizing the electrode area is to arrange an electrode surface perpendicularly to the radius direction of the PET imaging apparatus 1. According to the above consideration, the lower limit value of one side of the electrode is 2 mm and the lower limit value of the electrode area s is 4 square millimeters.

In the above explanation, the semiconductor material S interacting with a γ-ray was CdTe. It is needless to say that the semiconductor material S may be TlBr and GaAs. Further, although the words of "the laminated structure", "top layer" and "bottom layer" were used, the words are used with reference to FIG. 7. When FIG. 7 is seen after being rotated by 90°, "the laminated structure" may be replaced with a "parallel structure" and the "top and bottom layers" may be replaced with "right and left layers." The direction of γ-ray incidence may be from the top, bottom, left, or right of FIG. 7. In other words, the detector 21 is configured so that the plurality of (e.g., five) semiconductor material S are arranged in parallel in such a manner as to be sandwiched between the cathode C and the anode A.

(Combined Substrate)

Figure 11:
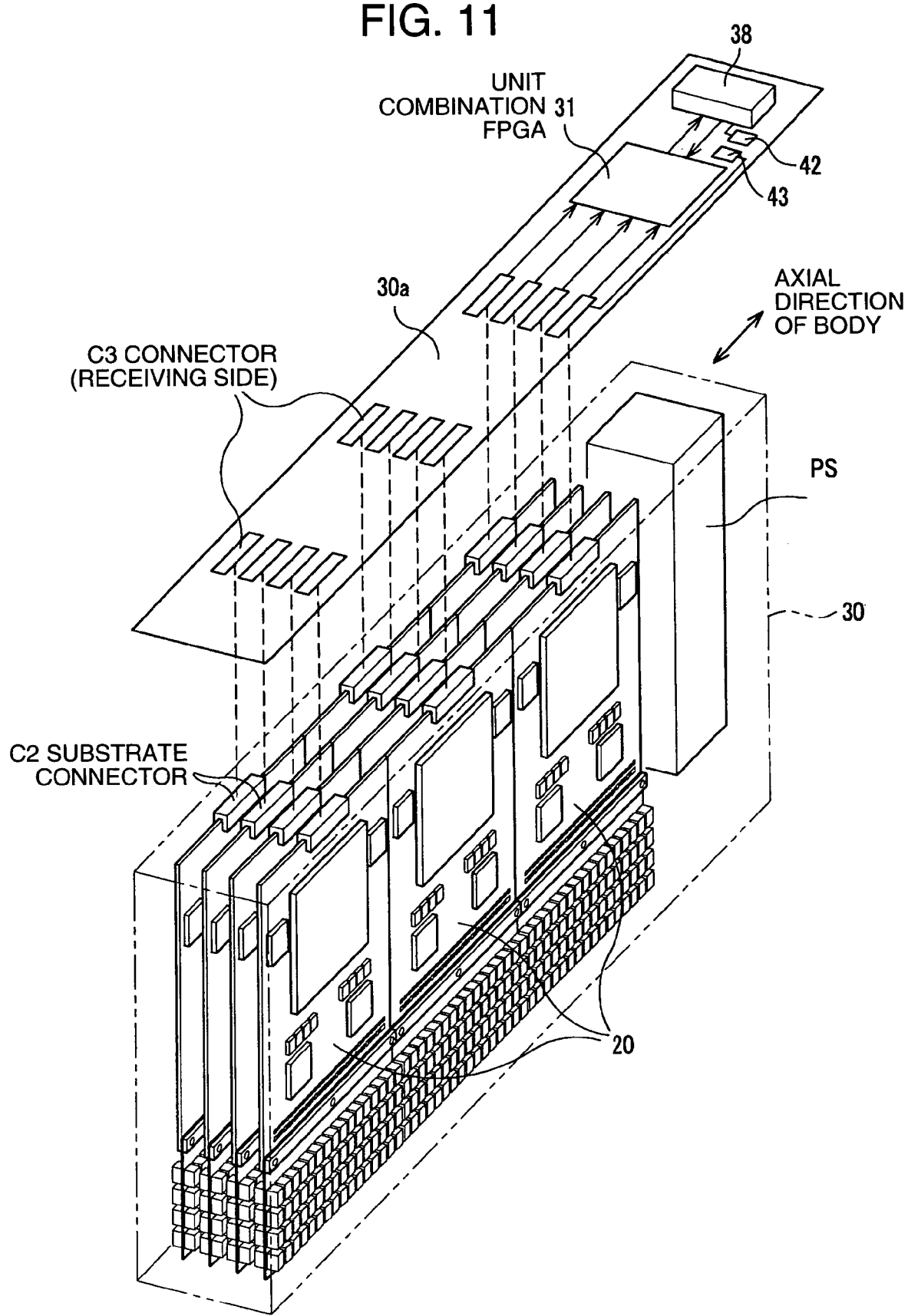
FIG. 11 is a perspective view cited for explaining the structure of a detector unit which stores a plurality of semiconductor radiation detectors.

Referring to FIG. 8, the following will describe the detailed structure of the combined substrate (unit substrate) 20 mounted in the detector unit 2 (FIG. 11). The combined substrate 20 has a detector substrate (first substrate) 20A having the plurality of detectors 21, and an ASIC substrate (second substrate) 20B having capacitors 22, resistors 23, analog ASICs 24, analog/digital converters (AD converters, hereinafter referred to as ADC) 25, a digital ASIC 26.

(Detector Substrate)

Figure 8A:
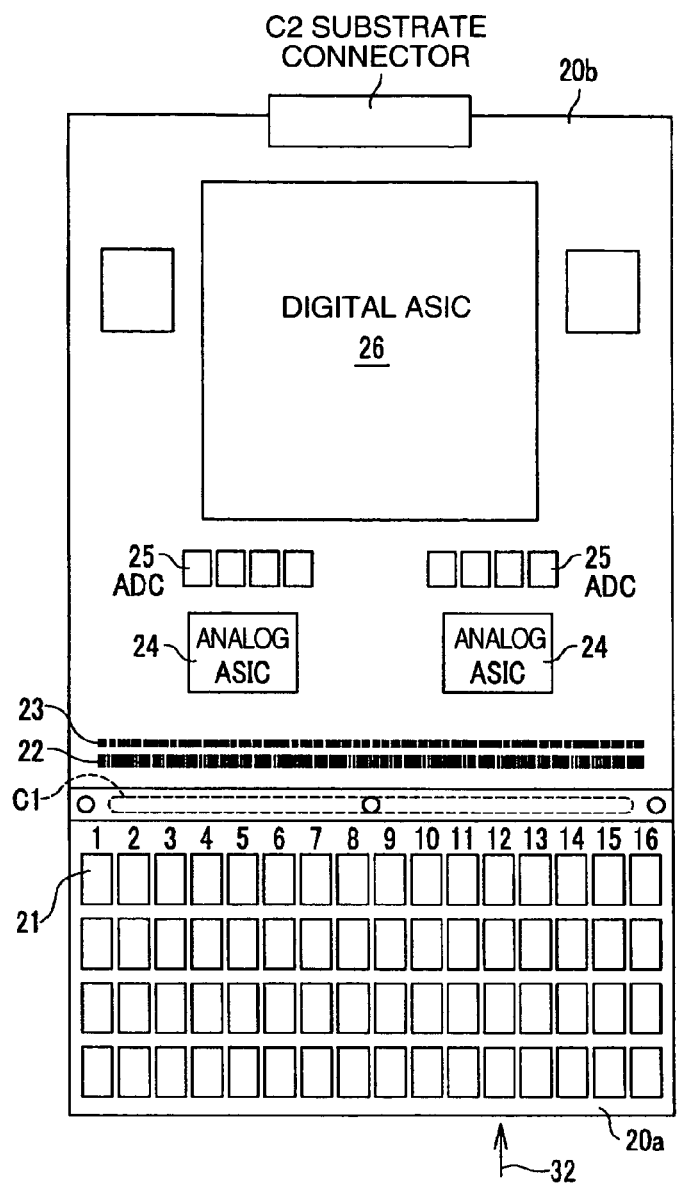
FIG. 8A is a front view showing a combined substrate in which a detector substrate and an ASIC substrate of the semiconductor radiation detector of the present embodiment are combined.
Figure 8B:
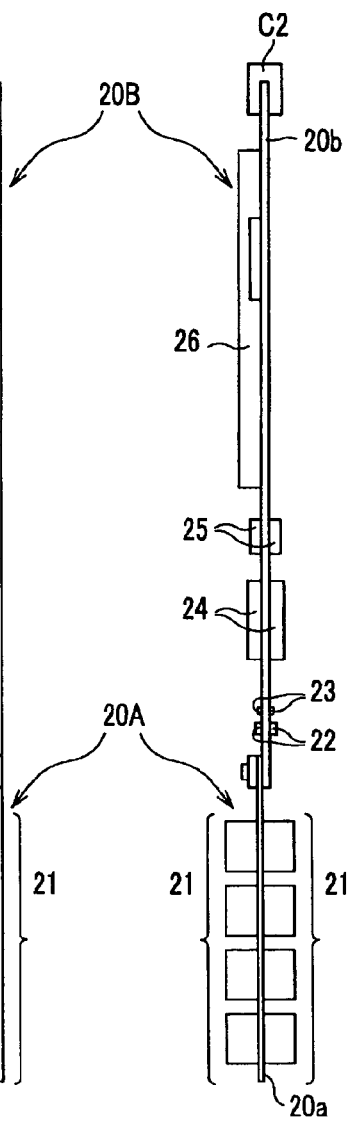
FIG. 8B is a side view of FIG. 8A.
Figure 8C:
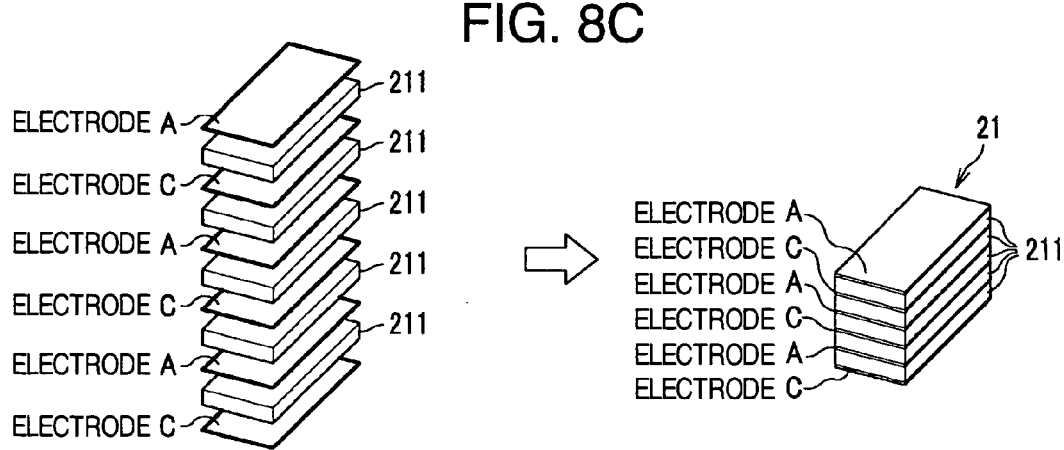
FIG. 8C is a perspective view schematically showing the configuration of the semiconductor radiation detector mounted on a detector substrate of FIG. 8A.

Referring to FIGS. 8A-8C, the detector substrate 20A having the detectors 21 will be described below. As shown in FIG. 8A, in the detector substrate 20A, the plurality of detectors 21 are arranged and mounted (packaged) in a lattice pattern on one side of the substrate body 20a (four lines of the 16 detectors 21, that is, 4×16=64 in total). In the radius direction of the PET imaging apparatus 1, four lines of the detectors 21 are arranged on a substrate body 20a. The above-described 16 detectors 21 are arranged in the axial direction of the PET imaging apparatus 1, that is, in the longitudinal direction (directions of moving forward and backward) of the bed 14. Further, as shown in FIG. 8B, the detectors 21 are attached on both sides of the detector substrate 20A and thus each of the detector substrates 20A has a total of 128 detectors 21. As the attached detectors 21 increases in number, γ-rays can be more readily detected with higher accuracy of position. Thus, the detectors 21 are arranged on the detector substrate 20A as densely as possible. Incidentally, when γ-rays radiated from the examinee H (FIG. 3) on the bed 14 move from below to above (the direction of an arrow 32, i.e., the radius direction of the PET imaging apparatus 1) in FIG. 8A, it is preferable to arrange the detectors 21 densely in the lateral direction of the detector substrate 20A in order to reduce the number of γ-rays passing though the detectors 21 (the number of γ-rays passing through gaps between the detectors 21). Hence, it is possible to improve the efficiency of detecting γ-rays, thereby increasing the spatial resolution of an obtained image.

As shown in FIG. 8B, the detector substrate 20A of the present embodiment has the detectors 21 attached to both sides of the substrate body 20a. Thus, unlike a detector substrate having detectors only on one side, the substrate body 20a can be used in a shared manner by mounting the detectors 21 on both sides. Hence, it is possible to reduce the number of the substrate bodies 20a by half and arrange the detectors 21 more densely in the circumferential direction. In addition, as described above, since the number of the detector substrates 20A (combined substrates 20) can be reduced by half, it is possible to save time and trouble to attach the combined substrates 20 to a housing 30 (FIG. 11), which will be discussed later.

In the above explanation, the 16 detectors 21 across the substrate are arranged in the axial direction of a camera 11. The configuration is not particularly limited. For example, the 16 detectors 21 across the substrate may be arranged in the circumferential direction of the camera 11.

As shown in FIG. 8C, each of the detectors 21 has a laminated structure where the single crystals of the semiconductor material S (sensor 211) are laminated like above-described thin plates. A supplementary explanation will be given below about the configuration and operation which have been discussed with reference to FIG. 7. As described above, the detector 21 has the anodes A and the cathodes C. A potential difference (voltage) such as 300 V is set across the anode A and the cathode C in order to collect charge. This voltage is supplied from the ASIC substrate 20B to the detector substrate 20A via a connector C1 (FIG. 8A). Further, a signal detected by the detector 21 is supplied to the ASIC substrate 20B via the connector C1. Hence, in the substrate body 20a of the detector substrate 20A, a intra-substrate wiring (not shown, for collecting charge and for transmitting and receiving a signal) which connect the connector C1 and the detectors 21, are provided. Besides, the intra-substrate wiring has a multilayered structure. In the present embodiment, the sensors 211 of the detector 21 are arranged in parallel with the substrate body 20a. The detector 21 may be attached so that the sensors 211 are arranged perpendicularly to the substrate body 20a.

(ASIC Substrate)

The ASIC substrate 20B having the ASIC will be described below. As shown in FIG. 8A, the ASIC substrate 20B has the two analog ASICs 24 and one digital ASIC 26 on one side of the substrate body 20b. As shown in FIG. 8B, since the analog ASICs 24 are attached on both sides of the substrate body 20b, the ASIC substrate 20B has a total of four analog ASICs 24. Further, the ASIC substrate 20B has the eight (=4×2) ADCs 25 on one side of the substrate body 20b and the 16 ADCs 25 on both sides of the substrate body 20b. Moreover, on both sides of the substrate body 20b, the capacitors 22 and the resistors 23 are arranged as many as the detectors 21. Like the detector substrate 20A, the ASIC substrate 20B (substrate body 20b) has intra-substrate wiring (not shown) to electrically connect the capacitors 22, the resistors 23, the analog ASICs 24, the ADCs 25, and the digital ASIC 26. The intra-substrate wiring also has a laminated structure.

In the arrangement (intra-substrate wiring) of the elements 22, 23, 24, 25, and 26, a signal supplied from the detector substrate 20A is sent to the capacitors 22, the resistors 23, the analog ASICs 24, the ADCs 25, and the digital ASIC 26 in this order.

Additionally, the ASIC substrate 20B has the connector (spiral contact) C1 which is connected to the intra-substrate wiring connected to the capacitors 22 and makes an electrical connection with the detector substrate 20A, and a substrate connector C2 which makes an electrical connection with the data processing apparatus (integrated FPGA, described later).

Incidentally, the above-described detector substrate 20A also has the connector C1 which is connected to the intra-substrate wiring connected to the detectors 21. The analog ASIC is an ASIC (Application Specific Integrated Circuit) which is a kind of LSI and is an IC for a specific application of processing an analog signal.

(Connecting Structure of the Detector Substrate and the ASIC Substrate)

The following will describe the connecting structure of the detector substrate 20A and the ASIC substrate 20B.

Instead of connecting the detector substrate 20A and the ASIC substrate 20B by butt-joining the end faces (ends), as shown in FIG. 8B, overlapping portions are provided near the ends to connect the connectors C1 attached to the overlapping portions. This connection is made in a detachable/attachable manner (is freely separated and connected) by a fastening screw. Such a connection is made for the following reason: when one or both ends of the combined substrate 20 is horizontally supported, which has the detector substrate 20A and the ASIC substrate 20B connected (joined) to each other, force distorting or bending down the combined substrate 20 is applied to the center (connected part) of the combined substrate 20. When the connected part has butted end faces, the connected part is readily distorted or bent. Hence, butted-joined end faces are not preferable.

In consideration of this point, in the present embodiment, instead of connecting the detector substrate 20A and the ASIC substrate 20B by butt-joining the end face, a connection is made by providing the overlapping portions where the ends overlap each other as described above. Thus, as compared with the butt-joined end faces, such a connection is preferable because a resistance to distortion and bending is improved. When the combined substrate increases the resistance to distortion and bending, for example, the displacement of the detector 21 is reduced so as to prevent a reduction in the accuracy of locating the occurrence of a γ-ray. As shown in FIG. 3, the PET imaging apparatus 1 has a number of detector units 2 (FIG. 11) which have the combined substrates 20 of FIG. 8A and are arranged like a donut. Thus, the combined substrates 20 disposed at 3 o'clock and 9 o'clock positions in the horizontal direction of FIG. 3 are readily distorted or bent. For this reason, it is important for the combined substrate 20 to obtain resistance to distortion and bending.

The detector substrate 20A and the ASIC substrate 20B are electrically connected to each other by using the overlapping portions as described above. Thus, the connector C1 (FIG. 8A) for electrically connecting the intra-substrate wirings of the substrates 20A and 20B is provided on each of the overlapping portions of the detector substrate 20A and the ASIC substrate 20B of FIG. 8B. For example, a spiral contact (R) is used as the connector C1 to preferably make an electrical connection. The spiral contact (R) is characterized in that a connecting terminal shaped like a ball makes contact with a spiral contact through a wide area so as to preferably make an electrical connection. When the connecting terminal shaped like a ball is provided on the ASIC substrate 20B, the spiral contact is provided on the detector substrate 20A. When the connecting terminal shaped like a ball is provided on the detector substrate 20A, the spiral contact is provided on the ASIC substrate 20B.

Since the detector substrate 20A and the ASIC substrate 20B are electrically connected to each other in such a manner, a signal can be transmitted from the detector substrate 20A to the ASIC substrate 20B with low loss. Lower loss increases, for example, the energy resolution of the detector 21.

As described above, the detector substrate 20A and the ASIC substrate 20B are connected to each other via a screw and the like in a detachable/attachable manner. Therefore, for example, even when the detectors 21 and the ASICs 24 and 26 have defects, it is only necessary to replace defective parts. Thus, it is possible to eliminate waste of the replacement of the overall combined substrate 20 even in the event of a defective part. Further, the detector substrate 20A and the ASIC substrate 20B are electrically connected to each other via the connector C1 such as the above-described spiral connector (R), thereby readily connecting/disconnecting (coupling/decoupling) the substrates.

In the above configuration, one detector substrate 20A is connected to the ASIC substrate 20B. The detector substrate may be divided into two or more. For example, the following configuration is applicable: the detectors 21 in eight columns and four rows are packaged on one substrate and two detector substrates are connected to the ASIC substrate. In this configuration, when one of the detectors 21 is failed, it is only necessary to replace the detector substrate having the failed detector out of the two detector substrates, thereby reducing waste in maintenance (reducing cost).

(Layout of Elements)

Figure 9:
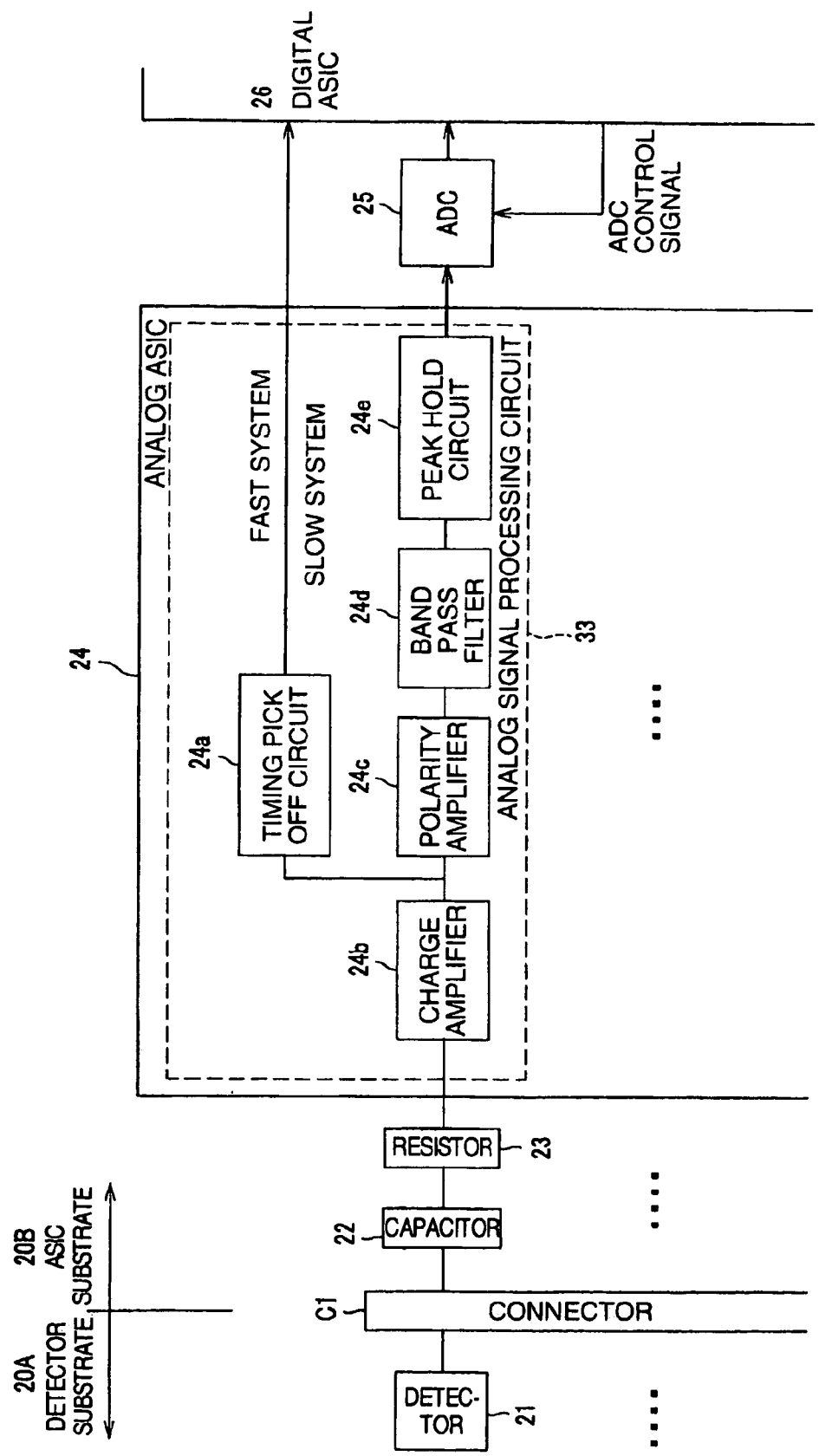
FIG. 9 is a block diagram schematically showing an analog detection circuit.

Referring to FIGS. 8A and 9, the following will describe the layout of the elements such as the detectors 21 and the ASICs 24 and 26 on the combined substrate 20.

As shown in FIG. 9, the detector 21 is connected to the analog ASIC 24 via the connector C1, the capacitor 22, and the resistor 23 by using electrical wiring (not shown). A detection signal of a γ-ray detected by the detector 21 passes through the capacitor 22 and the resistor 23 via the electrical wiring and is processed in the analog ASIC 24. Further, the signal processed in the analog ASIC 24 is processed in the ADC 25 and the digital ASIC 26.

Figure 10:
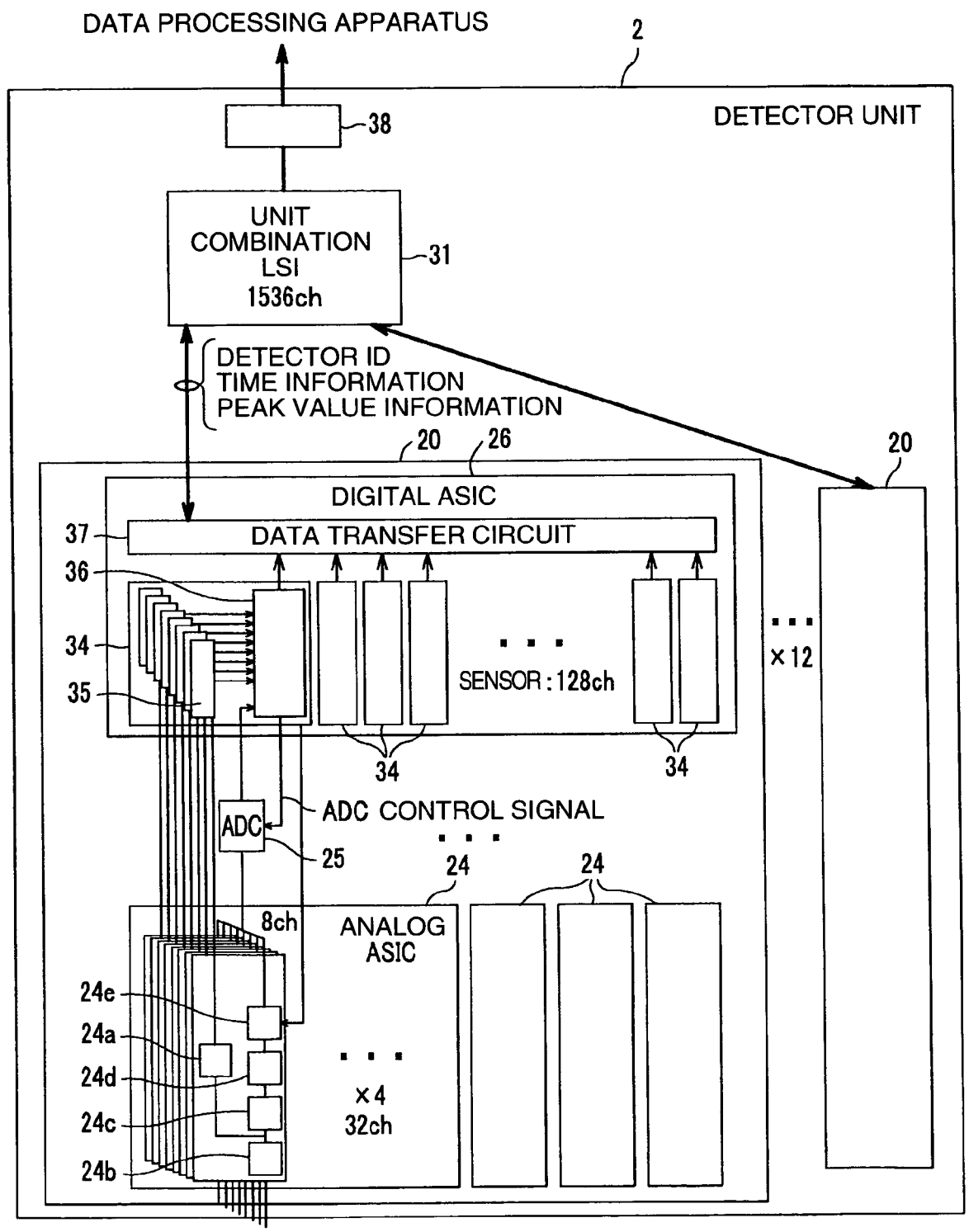
FIG. 10 is a block diagram which schematically shows the configuration of a digital ASIC and the connection relationship between an analog ASIC and the digital ASIC.

In this case, a short circuit and short wiring (distance) are preferable because the influence of noise and the attenuation of a signal are reduced in the processing. Further, when a coincidence detection is conducted in the PET imaging apparatus 1, a shorter circuit and shorter wiring are preferable because a delay is reduced (preferable because the accuracy of detection time is not reduced). Thus, in the present embodiment, the detectors 21, the capacitors 22, the resistors 23, the analog ASICs 24, the ADCs 25, and the digital ASIC 26 are arranged (laid out) in this order from the axis to the outside in the radius direction of the PET imaging apparatus 1 as shown in FIG. 8A. This order is the same as the signal processing order performed by the elements 21, 22, 23, 24, 25, and 26 (FIGS. 9 and 10). That is, from the axis of the camera 11 to the outside, "detectors, analog integrated circuits, AD converters, and a digital integrated circuit are arranged in this order on a substrate and wiring is carried out in this order." In other words, the order of arranging the elements 21, 22, 23, and 24 from the detectors 21 to the digital ASIC 24 matches with the signal processing order of the elements 21, 22, 23, and 24. Hence, a weak signal detected by the detector 21 can be transmitted to the analog ASIC 24 by reducing the length of the wiring (distance).

Since processing such as the amplification of a signal is performed in the analog ASIC 24, even when wiring after the analog ASIC 24 is long, a signal is less susceptible to noise. That is, in consideration of noise, no problem occurs even if wiring after the analog ASIC 24 is long. However, as described above, long wiring delays the transmission of a signal and thus the accuracy of detection time may be reduced.

In the present embodiment, since one combined substrate 20 includes the analog ASICs 24 and the digital ASIC 26 as well as the detectors 21, it is possible to arrange the detectors 21, the analog ASICs 24, and the digital ASIC 26 in the perpendicular direction of the bed 14, that is, orthogonally to the body axis of the examinee H to be examined. Thus, the length of the PET imaging apparatus 1 in the longitudinal direction of the bed 14 does not have to be increased more than necessary. It can be considered that the analog ASICs 24 and digital ASICs 26 is disposed along the longitudinal direction of the bed 14 on the outer side of the radius direction of the detectors arranged like a ring. However, the PET imaging apparatus 1 becomes longer than necessary in the longitudinal direction of the bed 14. Moreover, a semiconductor radiation detector is used as the detector 21, and the analog ASIC 24 and the digital ASIC 26 are used as signal processors. Thus, it is possible to reduce a length in the longitudinal direction of the combined substrate 20 and considerably reduce a length in the orthogonal direction of the PET imaging apparatus 1 as compared with the case where a scintillator is used. Further, since the combined substrate 20 has the detectors 21, the analog ASICs 24, and the digital ASIC 26 which are arranged in this order along the longitudinal direction of the combined substrate 20, the wiring for connecting the elements can be shortened and the wiring of the substrate can be simplified. Therefore, it is possible to achieve the PET imaging apparatus 1 contributing to miniaturization.

In the present embodiment, one analog ASIC 24 is connected to the 32 detectors 21 to process signals obtained from the detectors 21. As shown in FIGS. 9 and 10, one analog ASIC 24 comprises 32 sets of analog signal processing circuits (analog signal processing apparatus) 33 made up of a slow system and fast system. The analog signal processing circuit 33 is provided for each of the detectors 21 and is connected to one detector 21. The fast system comprises a timing pick off circuit 24a to output a timing signal for identifying a detection time of γ-rays. The slow system comprises a charge amplifier (preamplifier) 24b, a polarity amplifier (linear amplifier) 24c, a band pass filter (waveform shaping apparatus) 24d and a peak hold circuit (peak value holding apparatus) 24e connected in this order for the purpose of calculating a peak value of the detected γ-rays. Note that the slow system is named "slow" because it takes a certain degree of processing time to calculate a peak value. A γ-ray detection signal outputted from the detector 21 and passed through the capacitor 22 and resistor 23 is amplified in the charge amplifier 24b and polarity amplifier 24c. The amplified γ-ray detection signal is passed through the band pass filter 24d and inputted to the peak hold circuit 24e. The peak hold circuit 24e holds a maximum value of the detection signal, that is, the peak value of a γ-ray detection signal proportional to energy of the detected γ-rays. One analog ASIC 24 is an LSI which integrates 32 sets of analog signal processing circuits 33.

The capacitor 22 and resistor 23 can also be provided inside the analog ASIC 24, but this embodiment arranges the capacitor 22 and resistor 23 outside the analog ASIC 24 for reasons such as obtaining an appropriate capacitance and appropriate resistance and reducing the size of the analog ASIC 24. The capacitor 22 and resistor 23 are preferably disposed outside because variations in the individual capacitance and resistance are reduced.

In the analog ASIC 24 shown in FIG. 9, the output of the slow system of this analog ASIC 24 is supplied to the ADC (analog/digital converter) 25 in the present embodiment. Moreover, the output of the fast system of the analog ASIC 24 is designed to be supplied to the digital ASIC 26.

The analog ASIC 24 and each ADC 25 are connected via one wire which sends slow system signals corresponding to 8 channels all together. Furthermore, each analog ASIC 24 and digital ASIC 26 are connected via 32 wires which send 32-channel fast system signals one by one. That is, one digital ASIC 26 is connected to four analog ASICs 24 via a total of 128 wires.

The output signal of the slow system outputted from the analog ASIC 24 is an analog peak value (maximum value of the graph shown in FIG. 5). Further, the output signal of the fast system outputted from the analog ASIC 24 to the digital ASIC is a timing signal indicating timing corresponding to the detection time. Of these signals, the peak value which is the slow system output is inputted to the ADC 25 via the wire (wire uniting 8 channels into one as described above) connecting the analog ASIC 24 and ADC 25 and is converted to a digital signal by the ADC 25. The ADC 25 converts a peak value to, for example, an 8-bit (0 to 255) digital peak value (e.g., 511 KeV→255). Moreover, a timing signal serving as the output of the fast system is supplied to the digital ASIC 26 via the wire connecting the analog ASIC 24 and digital ASIC 26.

The ADC 25 sends the digitized 8-bit peak value information to the digital ASIC 26. For this purpose, each ADC 25 and digital ASIC 26 are connected via a wire. For example, since there are 16 ADCs 25 on both sides, the digital ASIC 26 is connected to the ADC 25 via a total of 16 wires. One ADC 25 processes signals corresponding to 8 channels (signals corresponding to eight detection elements). The ADC 25 is connected to the digital ASIC 26 via a wire for transmitting an ADC control signal and a wire for transmitting peak value information.

As shown in FIG. 10, the digital ASIC 26 comprises a plurality of packet data generation apparatuses 34, each of which includes eight time decision circuits (time decision apparatuses) 35 and one ADC control circuit (ADC control apparatus) 36, and a data transfer circuit (data transmission apparatus) 37. All these elements are integrated into one LSI. All the digital ASICs 26 provided in the PET imaging apparatus 1 receive a 500 MHz clock signal from a clock generation apparatus (crystal oscillator, not shown) and operates synchronously. The clock signal inputted to each digital ASIC 26 is inputted to the respective time decision circuits 35 in all the packet data generation apparatuses 34. The time decision circuit 35 is provided for each of the detectors 21 and receives a timing signal from the timing pick off circuit 24a of the corresponding analog signal processing circuit 33. The time decision circuit 35 determines the detection time of γ-rays based on the clock signal when the timing signal is inputted. Since the timing signal is based on the fast system signal of the analog ASIC 24, a time close to a real detection time can be set as the detection time (time information).

The ADC control circuit 36 receives a timing signal at which γ-rays are detected from the time decision circuit 35 and identifies the detector ID. That is, the ADC control circuit 36 stores a detector ID corresponding to each time decision circuit 35 connected to the ADC control circuit 36 and can identify, when time information is inputted from a certain time decision circuit 35, the detector ID corresponding to the time decision circuit 35. This is possible because the time decision circuit 35 is provided for each of the detectors 21. Moreover, after inputting the time information, the ADC control circuit 36 outputs an ADC control signal including detector ID information to the ADC 25. The ADC 25 converts, to a digital signal, the peak value information outputted from the peak hold circuit 24e of the analog signal processing circuit 33 corresponding to the detector ID, and the ADC 25 outputs the information. The peak value information is inputted to the ADC control circuit 36. The ADC control circuit 36 adds the peak value information to the time information and detector ID to create packet data. The packet data (including detector ID, time information, and peak value information) outputted from the ADC control circuit 36 of each packet data generation apparatus 34 is inputted to the data transfer circuit 37.

The data transfer circuit 37 sends packet data, which is digital information outputted from the ADC control circuit 36 of each packet data generation apparatus 34, to the integrated circuit (unit combination FPGA (Field Programmable Gate array) 31) for unit combination that is provided for the housing 30 of the detector unit 2 (FIGS. 11 and 12) which houses twelve combined substrates 20, for example, periodically. The unit combination FPGA (hereinafter referred to as "FPGA") 31 outputs the digital information to an information transmission wire connected to the connector 38.

In this way, packet data which is outputted from the digital ASIC 26 and includes detector IDs for uniquely identifying (1) peak value information, (2) determined time information and (3) detector 21 is sent to a PET data processing section 12a (FIG. 16) of the data processing apparatus 12 (FIG. 1) of the subsequent stage through the information transmission wire. The coincidence detection apparatus 12A of the PET data processing section 12a carries out coincidence detection processing (when two γ-rays with predetermined energy are detected with a time window with a set time, this processing regards these γ-rays as a pair of γ-rays generated by annihilation of one positron) based on the packet data sent from the digital ASIC 26, counts the simultaneously measured pair of γ-rays as one γ-ray and locates, by using the detector IDs, the two detectors 21 which have detected the pair of γ-rays. When there are three or more γ-ray detection signals detected within the above time window (when there are three or more detectors 21 which have detected γ-rays), the PET data processing section 12a identifies the two detectors 21 into which γ-rays are incident first out of three or more detectors 21 using peak value information, etc., on these γ-ray detection signals. The identified pair of detectors 21 is simultaneously measured and one count value (first information) is generated. Further, a tomographic information creation apparatus 12B of the PET data processing section 12a creates tomographic information on the examinee at the position where radiopharmaceuticals are concentrated, that is, position of malignant tumor, using count values obtained by coincidence detection and position information (second information) on the detectors 21. This tomographic information is displayed on the display apparatus 13. Information such as the above digital information, count values obtained by coincidence detection, position information on the detectors 21 and tomographic information are stored in the storage apparatus of the data processing apparatus 12.

In the above described explanations, the detector substrate 20A has the detectors 21 and the ASIC substrate 20B has the capacitors 22, the resistors 23, the analog ASICs 24, the ADCs 25, and the digital ASIC 26. The detector substrate (first substrate) 20A may have the detectors 21, the capacitors 22, the resistors 23, and the analog ASICs 24, etc., and the ASIC substrate (second substrate) 20B may have the ADCs 25 and the digital ASIC 26, etc. By the detector substrate 20A having the detectors 21 and the analog ASICs 24, the distance (wire length) between the detector 21 and analog ASIC 24 can be further shortened. Thus, it is possible to further reduce the influence of noise.

Furthermore, the combined substrate 20 may include three substrates (detector substrate 20A, analog ASIC substrate and digital ASIC substrate) which may be connected in a detachable/attachable manner through their respective connectors. The detector substrate 20A has the detectors 21, the analog ASIC substrate has the capacitors 22, the resistors 23, and the analog ASICs 24, and the digital ASIC substrate has the ADCs 25 and the digital ASIC 26. This configuration separates the substrate incorporating the analog circuit from the substrate incorporating the digital circuit to prevent noise on the digital circuit side from entering the analog circuit. Moreover, this configuration separates the substrate incorporating the analog ASIC from the substrate incorporating the digital ASIC and connects the two substrates using a detachable/attachable connector, and therefore even when only the digital ASIC malfunctions, only the digital ASIC substrate needs to be replaced. In this way, this structure can further reduce waste.

In the above explanation, the substrate body 20a (detector substrate 20A) for mounting the detectors 21 is different from the substrate body 20b (ASIC substrate 20B) for mounting the ASICs 24, 26. Thus, when, for example, both ASICs are soldered to a substrate by means of a BGA (Ball Grid Array) using reflow, only the ASIC substrate can be soldered. This is preferable because it is not necessary to expose the detectors 21 to a high temperature. Of course, the connector C1 may be omitted when all the components 21 to 26 are placed on the same substrate.

(Unit Construction Through Housing of Combined Substrate)

The following will describe a unit construction where the combined substrate 20 is housed in the housing 30. In the present embodiment, 12 combined substrates 20 are housed in the housing (frame) 30 to constitute a detector unit (12 substrate units) 2. The PET imaging apparatus 1 is configured so that 60 to 70 detector units 2 are arranged in the circumferential direction in a detachable/attachable manner (FIG. 13B) so as to facilitate maintenance and examination.

(Placement in Housing)

As shown in FIG. 11, the detector unit 2 comprises a housing 30, etc., for housing or holding the 12 combined substrates 20, a high-voltage power supply PS for supplying a charge collecting voltage to the 12 combined substrates 20, the FPGA 31, signal connectors for exchanging signals with the outside, and power connectors for receiving a power supply from the outside.

Figure 12:
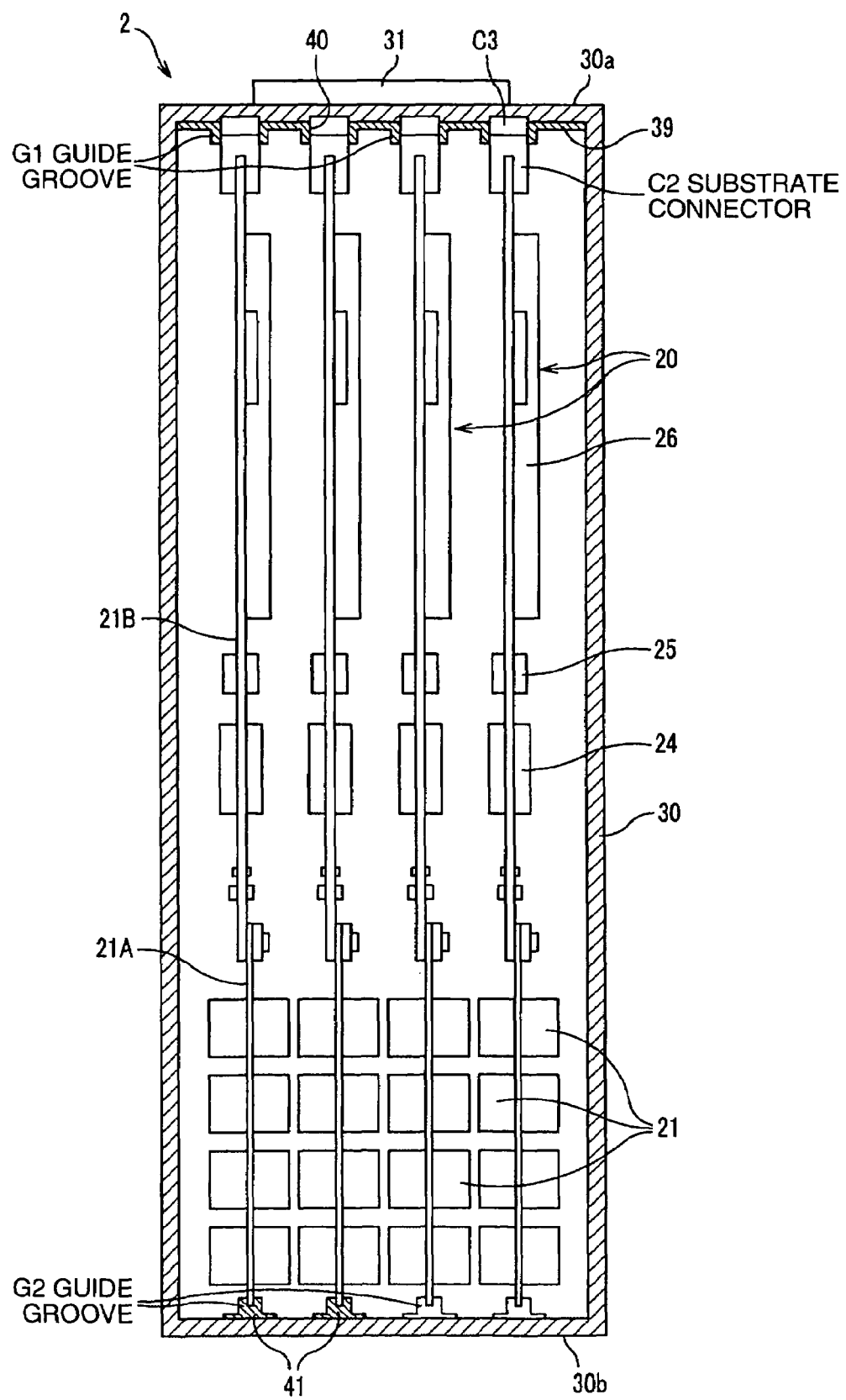
FIG. 12 is a side view showing that a side plate is removed from the detector unit of FIG. 11.

As shown in FIGS. 11 and 12, the combined substrates 20 are housed in the housing 30, arranged in three rows in the depth direction (longitudinal direction of the bed 14) without overlapping with one another and in four rows in the width direction (circumferential direction of the PET imaging apparatus 1). That is, one housing 30 houses 12 combined substrates 20. To realize such housing, a guide member 39 is disposed in the housing 30 and is attached to the upper end of the housing (cover) 30. The guide member 39 consists of four rows of guide grooves (guide rails) G1 which extend in the depth direction and are arranged at appropriate intervals in the circumferential direction. The guide member 39 has an opening 40 opposed to each connector C3 of a ceiling plate 30a in the portion of each guide groove G1. Further, a bottom surface 30b of the housing 30 is provided with four guide members 41 each of which has one guide groove (guide rail) G2 extending in the depth direction and are arranged at appropriate intervals in the circumferential direction (FIG. 12). The guide grooves G1 and G2 have a depth corresponding to a capacity of housing three combined substrates 20. An end of the combined substrate 20 on the ASIC substrate 20B side is housed in the guide groove G1 and an end of the combined substrate 20 on the detector substrate 20A side is housed in the guide groove G2. Three combined substrates 20 are held in the depth direction of the guide grooves G1, G2. Since the end of the combined substrate 20 on the ASIC substrate 20B side and the other end on the detector substrate 20A side slide in the guide grooves G1 and G2, the combined substrates 20 can be readily positioned at predetermined points by sliding the combined substrates 20 in the guide grooves G1 and G2 with fingers. In this case, each substrate connector C2 is disposed in the portion of each opening 40. After a predetermined number of combined substrates 20 are arranged in the housing 30, the ceiling plate 30a is attached at the top end of the housing 30 in a detachable/attachable manner using screws, etc. Each connector C3 provided on the ceiling plate 30a is inserted in the corresponding opening 40 and is connected to the corresponding substrate connector C2. The terms "upper" and "lower" parts of the housing 30 are applicable when the housing 30 is removed from the PET imaging apparatus 1, and when the housing 30 is mounted in the PET imaging apparatus 1 as shown in FIGS. 13A and 13B, the upper and lower parts may be inverted or turned 90 degrees to be "right" and "left" parts or located diagonally.

As shown in FIG. 12, the ceiling plate 30a of the housing 30 comprises not only the four rows of guide grooves G1 but also FPGA 31 and connector 38. The connector 38 is connected to the FPGA 31. The FPGA 31 is programmable in the field. In this aspect, the FPGA 31 is different from the ASIC which is not programmable. Therefore, as FPGA 31 with this embodiment, even if the number or type of the combined substrates 20 to be housed changes, it is possible to properly respond to changes in the number of substrates by programming in the field.

Since the detectors 21 containing CdTe as the semiconductor material S in this embodiment generate charge in reaction to light, the housing 30 is made of a material such as aluminum and an alloy of aluminum that have light shielding properties and the housing 30 is configured so as to eliminate gaps permitting the entry of light. That is, the housing 30 has light shielding properties. When light shielding properties are secured by other means, the housing 30 itself does not need light shielding properties and the housing 30 can be a frame (framework) to hold the detectors 21 in a detachable/attachable manner (e.g., no light shielding plane member (panel), etc., is necessary).

Figure 13A:
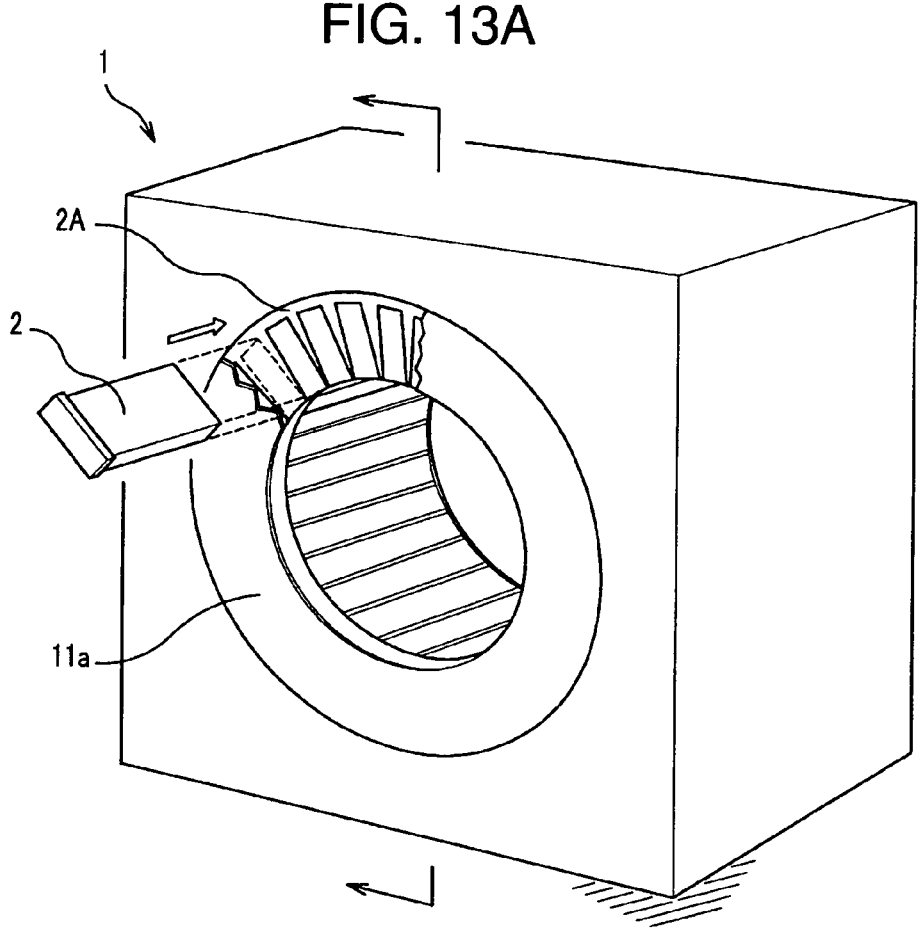
FIG. 13A is a partially cutaway perspective view showing a state of mounting the detector unit in the PET imaging apparatus.
Figure 13B:
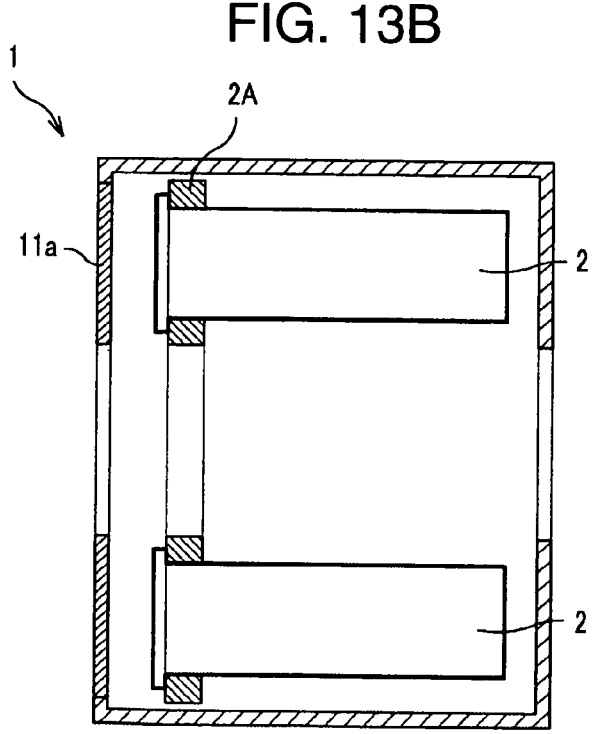
FIG. 13B is a sectional view showing the center of FIG. 13A.

As shown in FIG. 13A, the detector unit 2 is mounted via a unit support member 2A. Furthermore, as shown in FIG. 13B, the detector unit 2 is mounted in the PET imaging apparatus 1 with one end supported by the unit support member 2A. The unit support member 2A has a hollow disk (doughnut) shape and comprises many windows (as many as the detector units 2 to be mounted) in the circumferential direction of the PET imaging apparatus 1. In order to support the detector units 2 at one end, a flange portion serving as a stopper is provided on the front side in the axial direction of the housing 30 of the detector unit 2. The flange portions inside in the circumferential direction become obtrusive when the detector units 2 are arranged as dense as possible in the circumferential direction. Therefore, the obtrusive flange portions may be removed from the housing 30 to allow the flange portions outside in the circumferential direction to remain. Another unit support member 2A may be provided and both ends of the detector unit 2 may be supported by the two unit support members 2A.

When the detector units 2 is mounted in the PET imaging apparatus 1, a cover 11a is removed to make the unit support member 2A exposed and the detector units 2 are inserted from the exposed portion until the detector units 2 touch the flange portions. When the detector units 2 are inserted and mounted, the PET imaging apparatus 1 and the connectors of the detector units 2 are connected to each other, and signals and power supply are connected between the PET imaging apparatus 1 and the detector units 2.

(Power Supply)

The following will describe the high-voltage power supply apparatus PS for supplying voltage for collecting charge. As shown in FIG. 11, in the detector unit 2, the high-voltage power supply apparatus PS for supplying charge collection voltage to each of the detectors 21 is provided in a space formed inside the housing 30 on the back of the FPGA 31. This high-voltage power supply apparatus PS receives a low voltage power supply, boosts the voltage to 300 V using a DC-DC converter (means for boosting the voltage, not shown) and supplies the voltage to each of the detectors 21. For each of the combined substrates 20 (=detector substrates 20A), 64 detectors 21 are provided on one side and thus 128 detectors 21 are provided on both sides. Twelve such combined substrates 20 are housed in one housing 30 (that is, one detector unit 2). Thus, the high-voltage power supply apparatus PS supplies voltages to 128×12=1536 detectors 21.

Conventionally, a supply voltage of 300 V with extremely small fluctuations is supplied from a precision power supply apparatus in a remote place, but (1) when the distance from the precision power supply apparatus increases, a wider insulating structure for high voltage wiring is required (the insulating distance increases) accordingly and (2) the voltage fluctuates due to a temperature variation of the detectors 21, so that even the supply of a precise voltage from the precision power supply apparatus does not necessarily result in an expected precise voltage in the desired target detectors 21.

Further, to facilitate maintenance and examination, it is also considered that the detector unit 2 of the present embodiment comprises a power connector (not shown) and a high-voltage power line extending from the precision power supply apparatus is removed on the power connector. In the present embodiment, it is considered that a high-voltage power supply is supplied to the detector units 2 from the outside of the units 2 via the power connector. However, in the case of a high voltage of 300 V, the power connector increases in size in addition to the above described problem of insulation.

In the present embodiment, the high-voltage power supply apparatus PS built in the detector unit 2 is connected to an external low voltage (5 to 15 V) DC power supply through the power connector 42 and connector 38 provided on the ceiling plate 30a via power wiring. A high-voltage terminal of the high-voltage power supply apparatus PS is connected to twelve connectors C3, which are provided on the ceiling plate 30a through the connector 43 provided on the ceiling plate 30a, and is connected to electrodes C of the detectors 21 provided on the substrate body 20a through the connectors C2 of the combined substrates 20, power wiring (not shown) in the substrate body 20b, the connector C1 and power wiring (not shown) in the substrate body 20a. The connectors C1 and C2 include not only connectors for transmitting output signals of the detectors 21 but also connectors for power wiring. Since the high-voltage power supply apparatus PS boosts a low voltage applied from a direct-current power supply to 300 V using a DC-DC converter, it is possible to reduce the high-voltage section and thereby shorten the insulation distance. That is, this eliminates the necessity for using high-voltage wiring for a portion from the connector 42 to the DC power supply. Further, maintenance is facilitated. For the problem of fluctuations in voltage, the present embodiment comprises the high-voltage power supply apparatus PS having accuracy according to a voltage changed by a temperature, instead of the high-precision power supply apparatus. Thus, it is possible to eliminate the necessity for a high-precision power supply. Further, since it is a low voltage that is received from an external power supply, it is possible to use a small power connector for the connector 38. The small power connector increases the degree of freedom in the layout. Further, since the high-voltage power supply apparatus PS is arranged in a space formed in the housing 30 on the back side of the FPGA 31, the arrangement of the high-voltage power supply apparatus PS in the housing 30 makes the detector unit 2 more compact without upsizing. The high-voltage power supply apparatus PS may be directly connected to the power wiring provided on the substrate body 20a, via the connector instead of the ceiling plate 30a. The power connector may be separated from the output signal connector of the detector 21. This configuration prevents noise from entering the signal wiring from the power supply system.

Further, by reducing a supply voltage to the detector unit 2, it is possible to supply power to the high-voltage power supply apparatus PS at a low voltage through the unit combination FPGA 31 as with power supplies to the ASICs 24, 26. Moreover, the supply of power using the high-voltage power supply apparatus PS eliminates the necessity for insulation from the housing (GND).

The voltage supplied to the high-voltage power supply apparatus PS is boosted to 300 V by a DC-DC converter (not shown) in the high-voltage power supply apparatus PS and after boosting, passes through the ceiling plate 30a of the housing 30, and is supplied from the ASIC substrate 20B→ detector substrate 20A→ each of the detectors 21 for each of the combined substrates 20. That is, the housing 30 (ceiling plate 30a) comprises voltage supplying wiring (not shown) for supplying a voltage from the high-voltage power supply apparatus PS to each of the combined substrates 20. Further, each of the combined substrates 20 comprises voltage supplying wiring which supplies a voltage supplied from the high-voltage power supply apparatus PS to each of the detectors 21 via the substrate connector C2.

B. (X-ray CT Imaging Apparatus)

Figure 15:
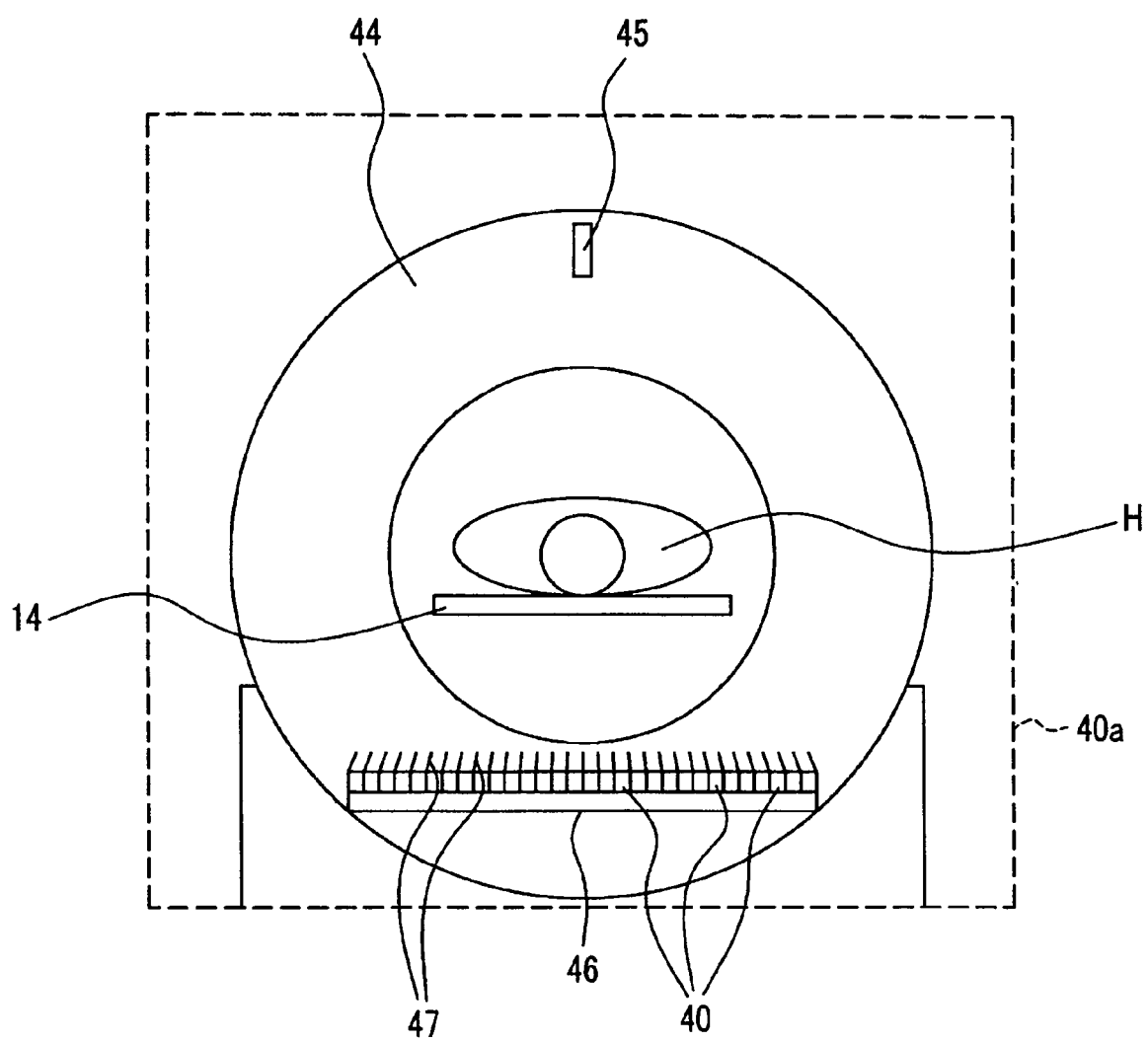
FIG. 15 is a diagram schematically showing a sectional view along the circumferential direction of the X-ray CT imaging apparatus shown in FIG. 14.

As shown in FIG. 1, the X-ray CT imaging apparatus 4 is disposed in the rear of the PET imaging apparatus 1. As shown in FIG. 14, the X-ray CT imaging apparatus 4 has radiation detectors 40, an X-ray source circumferential moving apparatus 41, a drive controller 42, an X-ray source controller 43, and a casing 40a (FIG. 15). Further, the X-ray source circumferential moving apparatus 41 comprises a disk-like holding part 44, an X-ray source 45, and an X-ray source apparatus holding part 45a. The X-ray source apparatus holding part 45a is attached to the outer surface of the disk-like holding part 44 on one end of the disk-like holding part 44. The X-ray source 45 is attached to the other end of the X-ray source apparatus holding part 45a.

The radiation detector 40 arranges an X-ray, which has passed through the examinee H from the X-ray source 45, on a detectable position. A plurality of (about 100) radiation detectors 40 are arranged from the disk-like holding part 44 via a detector holding part 46 and are rotated around the examinee H in synchronization with the X-ray source circumferential moving apparatus 41. Moreover, a collimator 47 is attached to the radiation detector 40 and only an X-ray generated from the X-ray source 45 is incident on the radiation detector 40. In the present embodiment, the radiation detector 40 is a scintillator detector.

The X-ray source 45 has a known X-ray tube (not shown). The X-ray tube comprises in a housing, an anode, a cathode, a current source of the cathode, and a voltage source for applying voltage across the anode and the cathode. The cathode is a filament made of tungsten. Electrons are released from the cathode by applying current from the current source to the cathode. The electrons are accelerated by voltage (140 kV) applied across the cathode and the anode from the voltage source and collide with the anode (W, Mo, etc.) serving as a target. X-rays of 140 keV or lower are generated when the electrons collide with the anode, and released form the X-ray source 45.

The X-ray source controller 43 controls the release time of X-rays from the X-ray source 45. That is, in an X-ray CT examination, the X-ray source controller 43 repeats the following control: an X-ray generating signal is outputted to close a switch (hereinafter referred to as an X-ray source switch, not shown) provided between the power supply and the anode (or cathode) of the X-ray tube in the X-ray source 45, an X-ray stop signal is outputted after first setting time to open the X-ray source switch, and the X-ray source switch is closed after second setting time. Across the cathode and the anode, voltage is applied during the first setting time but is not applied during the second setting time. With such control, X-rays are released like pulses from the X-ray tube.

At the start of an X-ray CT examination, the drive controller 42 outputs a drive start signal to close a switch (hereinafter referred to as a first motor switch, not shown) connected to the power supply. A first motor is rotated by supplying current, the turning force of the motor is transmitted to a pinion via a power transmission mechanism, and thus the pinion is rotated. The rotation of the pinion moves the disk-like holding part 44, that is, the X-ray source 45 around the examinee H at a predetermined speed. At the completion of the X-ray CT examination, the drive controller 42 outputs the drive stop signal to open the first motor switch. Thus, the X-ray source 45 is caused to stop moving in the circumferential direction. Since the radiation detectors 40 are fixed on the disk-like holding part 44 via the detector holding part 46, the radiation detectors 40 are rotated with the X-ray source 45. Hence, when X-rays are radiated from the X-ray source 45, the X-rays having passes through the examinee H are measured by the radiation detectors 40.

The drive start signal having been outputted from the drive controller 42 at the start of the X-ray CT examination is inputted to the X-ray source controller 43. The X-ray source controller 43 outputs an x-ray generating signal based on the input of the drive start signal. Thereafter, the X-ray stop signal and the X-ray generating signal are repeatedly outputted. In this way, since the X-ray stop signal and the X-ray generating signal are repeatedly outputted, the X-ray source 45 releases X-rays during setting time (e.g., 1 μsec) and then stops releasing X-rays. The release and stop of X-rays are repeated when the X-ray source 45 moves in the circumferential direction. The X-rays released from the X-ray source 45 are applied to the examinee H like fan beams. After passing through the examinee H, the X-rays are positioned apart from the X-ray source 45 and are detected by the radiation detectors 40 beyond the examinee H, rotated concurrently with the X-ray source. The radiation detectors 40 output the detection signals (hereinafter referred to as X-ray detection signals) of the X-rays.

The above explanation discussed the method of pulsed irradiation with X-rays. The method of irradiation is not particularly limited and thus X-ray may be applied continuously while charge accumulation time is controlled upon measurement.

(Data Processor)

Figure 16:
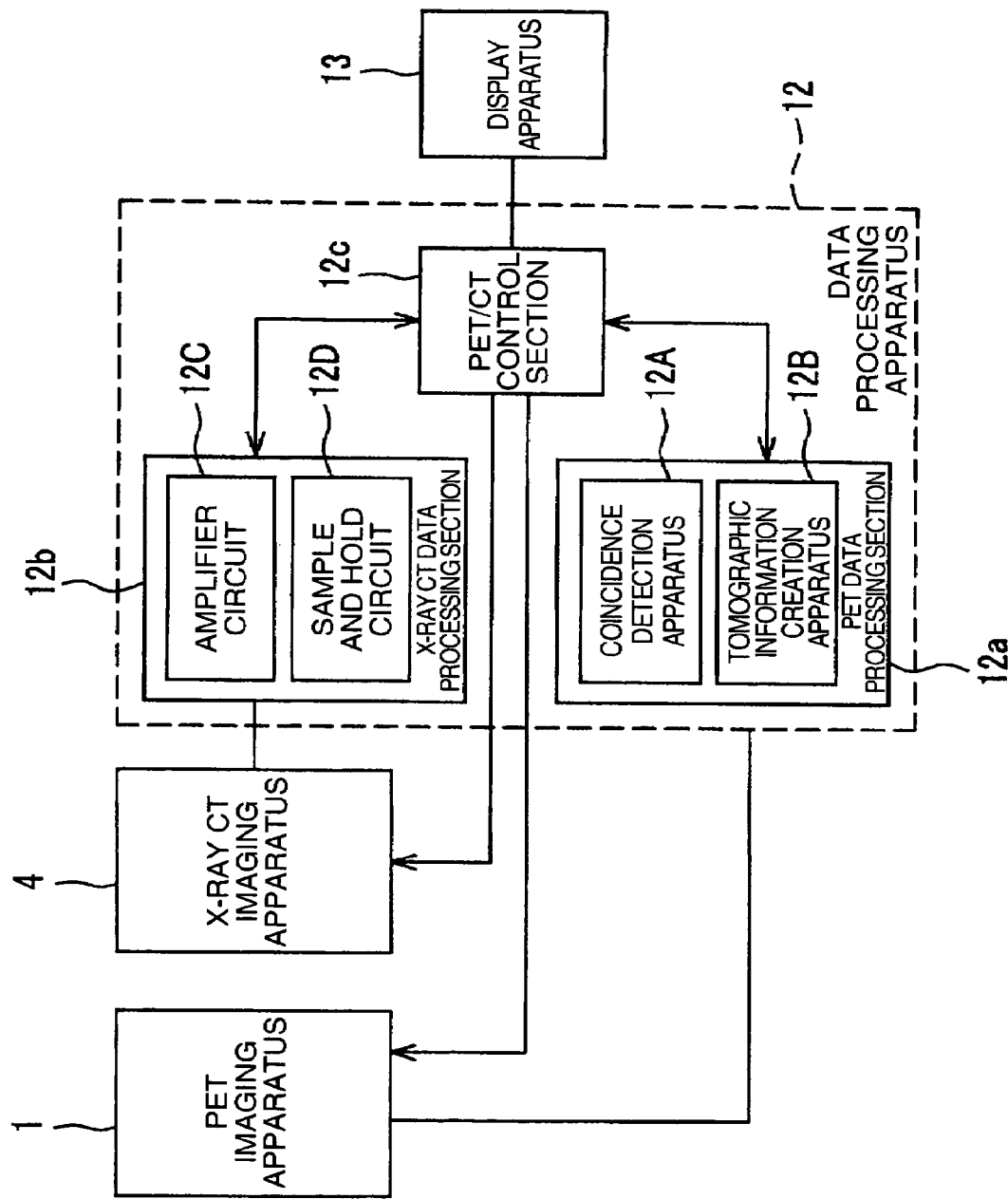
FIG. 16 is a block diagram schematically showing a data processing apparatus.

As shown in FIG. 16, the data processing apparatus 12 has the PET data processing section 12*a* for processing data from the PET imaging apparatus 1 and an X-ray CT data processing section 12*b* for processing data from the X-ray CT imaging apparatus 4. Further, the data processing apparatus 12 includes a PET/CT control section 12*c*.

The PET data processing section 12*a* has a storage apparatus (not shown), a coincidence detection apparatus 12A, and a tomographic information creation apparatus 12B. The PET data processing section 12*a* captures packet data including a peak value of detected γ-rays, data of detection time, and detector (channel) IDs. The coincidence detection apparatus 12A performs coincidence detection based on the packet data, particularly the data of detection time and the detector IDs, identifies the detection positions of 511 keV γ-rays, and stores the positions in the storage apparatus. The tomographic information creation apparatus 12B creates a functional image based on the identified positions and outputs the image. In the case of two-dimensional imaging, it is preferable to use a method such as filtered back projection as a PET image reconstruction method. In the case of three-dimensional imaging, an image is reconstructed by using, e.g., Fourier rebinning discussed in IEEE Transactions on Medical Imaging, vol. 16, page 145, 1997. Thus, a PET image is obtained. With the PET image, it is possible to obtain occurrence density information on a pair of γ-rays.

The X-ray CT data processing section 12*b* includes an amplifier circuit 12C and a sample and hold circuit 12D. The X-ray CT data processing section 12*b* receives the X-ray detection signal from the radiation detector 40 and converts the intensity of the X-ray detection signal into data. Since X-rays released from the X-ray source 45 are considerably higher in incidence rate than the γ-rays, the X-ray CT data processing section 12*b* is ordinarily constituted of a so-called current mode (integration mode) measuring circuit. X-ray detection signals (current signals) from the radiation detectors 40 are accumulated by the integral amplifier circuit 12C, and the sample values of the signals are held by the sample and hold circuit 12D. These operations are repeated by a reset signal in a predetermined period (maximum about several-ten milli-seconds), so that the intensity of X-rays is converted into data by the sample and hold circuit 12D in each fixed time. As in the above-described case, the method of reconstructing X-ray CT data is filtered back projection method which is described in IEEE transactions on Nuclear Science, NS-21 vol., page 21. An obtained image has CT values in a cube or a cube voxel which is set with equal sides in the x direction, y direction, and z direction in a body.

The PET/CT control section 12*c* is constituted of a computer or a work station and so on. The PET/CT control section 12*c* creates a timing chart of a PET examination and a CT examination therein, instructs the bed 14, the PET imaging apparatus 1, the X-ray CT imaging apparatus 4, the PET data processing section 12*a*, and the X-ray CT data processing section 12*b* to perform desired operations based on the timing chart, and reconstruct an X-ray CT image based on a tomogram (PET image) and X-ray imaging data from the X-ray CT data processing section 12*b* by using γ-ray imaging data from the PET data processing section 12*a*. When the X-ray CT image is obtained, a linear attenuation coefficient in the examinee H between the X-ray source 45 and the radiation detectors 40 is determined using a decrement of X-rays based on the X-ray imaging data. A linear attenuation coefficient of each voxel is determined by using the linear attenuation coefficient according to a method such as filtered back projection. Then, a CT value of each voxel is obtained using a linear attenuation coefficient of each voxel. The X-ray CT image data is obtained using these CT values. Further, an absorbed amount of γ-rays of 511 keV is calculated from the CT value, so that absorption in the body of the examinee H is corrected and a correct PET tomogram is reconstructed. The reconstructed tomograms are both displayed by the display apparatuses 13. Therefore, it is not necessary to provide a radiation source for correcting absorption in the PET imaging apparatus 1.

In this case, the PET image can be readily combined with the X-ray CT image with accuracy by aligning the axes of holes 50 (FIG. 2) in both of image data. The images may be combined in sinogram data and a frequency space. The combined tomograms which are displayed by the display apparatus 13 include an X-ray CT image. Thus, in the PET image, it is possible to readily confirm the position of an affected area in the body of the examinee H. That is, since the X-ray CT image includes the image of internal organs and bones, the position of an affected area (e.g., a cancer) can be identified based on the positional relationship between the internal organs and bones.

In the present embodiment, the PET imaging apparatus 1 and the X-ray CT imaging apparatus 4 are arranged along the length of the bed 14 (along the axial direction of the examinee H). Thus, it is possible to separately pick up the PET image from the PET imaging apparatus 1 and the X-ray CT image from the X-ray CT imaging apparatus 4 and prevents interference, etc., from losing necessary data.

(Operations of the Radiological Imaging System)

The following will describe the operations of the radiological imaging system configured thus.

Before a radiological examination, radioactive chemicals for PET are first administered beforehand to the examinee H by injection, etc., so that an administered radiation is 370 MBq in the body. The radioactive chemicals is selected according to the objective of examination (to locate a cancer or to conduct an examination of an aneurysm of a heart, etc.). The examinee H stands by until the radioactive chemical gathers so as to permit imaging. During a predetermined time, the radioactive chemicals gather on an affected area of the examinee H. After the predetermined time, the examinee H is laid down on the bed 14 (FIG. 2). In some kinds of examinations, radioactive chemicals may be administered to the examinee H laid down on the bed 14.

An examiner (a clinical radiographer and a doctor) who performs a PET examination and a CT examination inputs necessary information (an area desired as a tomogram (imaged area or concerned area), the number of slices, slicing intervals, the timing of CT scanning, an absorbed dose, etc.) to the PET/CT control section 12c according to the objective of the examination. The information input screen of FIG. 17 is displayed by the display apparatus 13 to input necessary data with a keyboard, a mouse, and so on. By arranging combo boxes and radio buttons on the screen as shown in FIG. 17, input can be readily performed. In PET/CT control, a PET examination/CT examination sequence (abbreviated as an "examination sequence" when necessary) is created based on the inputted information. When a "display button" is clicked on the information input screen of FIG. 17, the examination sequence is created in the PET/CT control section 12c and is displayed on the display apparatus 13. When a "start examination" button is clicked, an examination is started. In the PET/CT control section 12c, the following parameters are all programmed in a series of examination sequences and are performed at a time determined by the number of clocks relative to the reference time to start an examination.

(1) Start and stop of the PET imaging apparatus 1 and the X-ray CT imaging apparatus 4

(2) Turning around of the X-ray source 45, movement in the axial direction, and an amount of irradiation (tube current, tube voltage)

(3) Start and stop of the PET data processing section 12a and the X-ray CT data processing section 12b (4) Permission and prohibition of the transmission of γ-ray imaging data and X-ray imaging data (5) Movement control of the bed 14.

The sequences (including movement control of the bad 14) are made so as to switch imaging between the PET imaging apparatus 1 and the X-ray CT imaging apparatus 4.

Further, since the irradiation area of X-rays spreads in the axial direction, switching is performed while the radiation detectors 40 are arranged as a group of about ten detectors at the maximum in the axial direction. Incidentally, when the radiation detector 40 is in a square form of 5 mm by 5 mm, the ten radiation detectors 40 arranged in series have a side of 50 mm. The side of 50 mm matches the spread of X-rays in the axial direction (like a sector spreading with an angle of 5° in the axial direction).

First, the examinee H laid down on the bed 14 is moved to a predetermined position and the PET imaging apparatus 1 is started.

The PET data control section 12a is started in response to an instruction from the PET/CT control section 12c, and a PET examination is started. γ-rays radiated from the body of the examinee H are detected by the detectors 21 and are transmitted as γ-ray imaging data to the PET data control section 12c. In the PET data processing section 12a, the γ-ray imaging data is generated in the above-described manner and transmitted to the PET/CT control section 12c. According to the sequence, the PET examination is carried out for a while in this state. When predetermined imaging is completed, the PET imaging apparatus 1 is stopped.

Before a CT examination, the X-ray source 45 is driven to generate X-rays. The intensity of generating X-rays is stabilized at a predetermined value (tube current, tube voltage) and the X-ray source 45 is caused to stand by. Then, the bed 14 is moved to a predetermined position of the X-ray CT imaging apparatus 4 (FIG. 14).

The radiation detectors 40 included in an area irradiated with X-rays are connected to the X-ray CT data processing section 12b, the X-ray CT data processing section 12b is started, and X-ray imaging data is obtained. Since the X-ray source 45 radiates X-rays with a spread of about 5° in the axial direction and about 60° in the circumferential direction, a plurality of radiation detectors 40 included in an axial radiation area and a circumferential radiation area (both are not shown) are connected the x-ray CT data processing section 12a (the axial spread of 5° is processed at a time). The X-ray source 45 is rotated in the circumferential direction by the X-ray source circumferential moving apparatus 41, so that the X-ray source 45 is rotated to perform a CT examination.

Since the examination sequence is set so that the X-ray source 45 is rotated and the radiation detectors 40 are switched in a synchronous manner. A switching order is issued without detecting the position of the X-ray source 45. That is, the switching timing of the radiation detectors 40 can be set in a sequence program because the rotation start time and rotation speed (angular speed) of the X-ray source 45 are already known.

Thereafter, the X-ray source 45 stops irradiation, the X-ray CT imaging apparatus 4 is stopped, the bed 14 is moved to the initial position, and the PET/CT examination is completed.

The PET/CT control section 12c reconstructs a PET image by using γ-ray imaging data received from the PET data processing section 12a and reconstructs an X-ray CT image by using X-ray imaging data obtained from the X-ray CT data processing section 12b. Then, the reconstructed X-ray CT image is displayed on the display apparatus 13.

Effects of the present embodiment will be discussed below.

Figure 22:
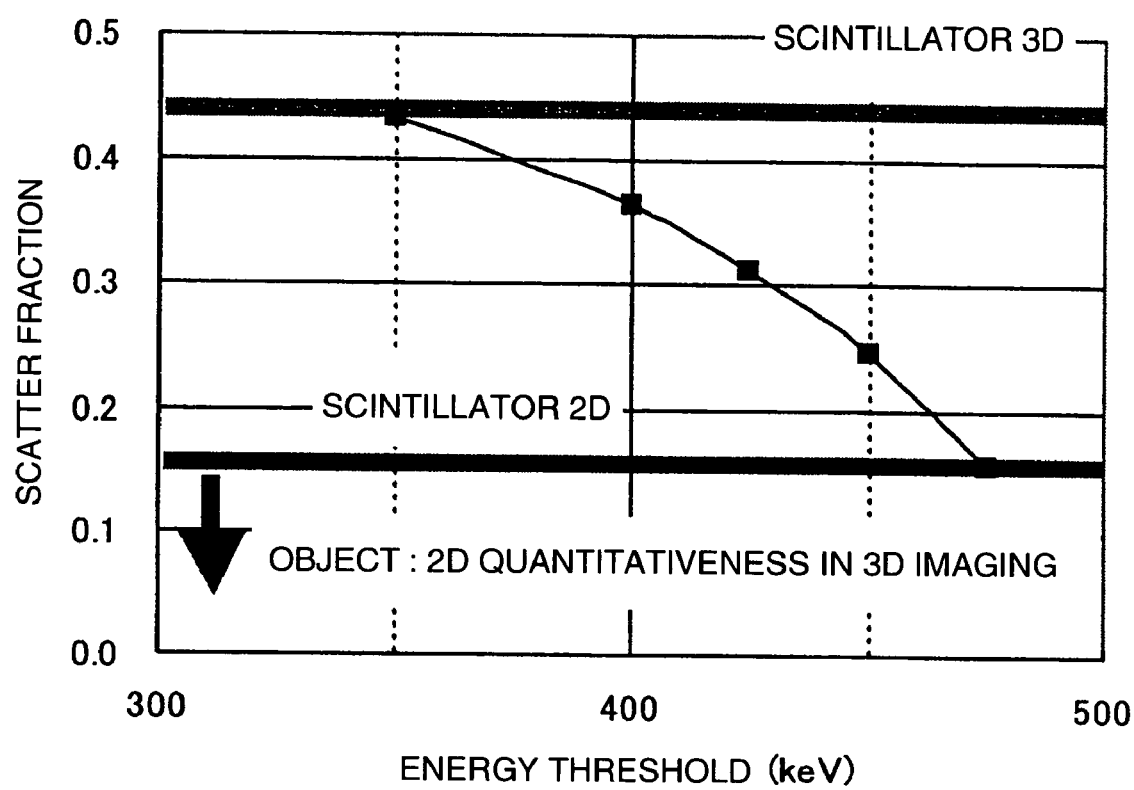
FIG. 22 is a graph which shows simulation results of 3D imaging and the relationship between an energy threshold value and a scatter fraction.

(1) In the present embodiment, energy resolution is improved and a scattered radiation is removed by using the semiconductor radiation detectors. Particularly in 3D imaging, it is possible to suppress an increase in scattered radiation, improve the quality of a PET image, and perform a quantitative examination. FIG. 22 shows simulation results of 3D imaging. FIG. 22 is the plot of the relationship between an energy threshold and a scatter fraction. The semiconductor radiation detector has an energy resolution of several percents, which can increase an energy threshold to about 475 KeV. It is found from FIG. 22 that an energy threshold value of 475 KeV can reduce a scatter fraction to about 20% or lower, which is comparable to that of 2D imaging, thereby achieving a highly quantitative examination.

(2) In the present embodiment, the position resolution is improved by using the semiconductor radiation detectors. Regarding the scintillator, signals from several tens of scintillators are amplified by a single photomultiplier and a scintillator position detected by calculating the center of gravity and so on, resulting in a degradation of the position resolution. Further, since the photomultiplier is used, there is a limit to a finer scintillator. On the other hand, in the PET imaging apparatus using the semiconductor radiation detectors of the present embodiment, the amplifier circuit is formed for each of the semiconductor radiation detectors, resulting in no degradation of the position resolution. Furthermore, the signal processing circuit is formed by using an ASIC and so on and thus it is possible to readily make fine the semiconductor radiation detectors and further improve the position resolution.

(3) In the present embodiment, the effect (1) enables a highly quantitative examination also in 3D imaging. Thus, it is possible to eliminate the need for 2D imaging and have a 3D-specific PET apparatus. Therefore, it is not necessary to set septa in the detectors, miniaturizing the apparatus.

(4) In the present embodiment, the semiconductor radiation detectors are used and the ASIC is used for signal processing. Thus, it is possible to miniaturize the semiconductor radiation detectors as compared with the photomultiplier used in the scintilator. Further, the semiconductor radiation detectors and the signal processing circuit are orderly arranged on the unit substrate, thereby achieving further miniaturization.

(5) In the present embodiment, the X-ray CT imaging apparatus and the PET imaging apparatus are arranged in series and CT values are used to correct absorption. Hence, it is not necessary to provide a source for absorption correction, so that the need for rotating the source inside the detector is eliminated and thus the apparatus is further miniaturized.

(6) In the present embodiment, the effects (1) to (5) can miniaturize the overall apparatus so that an examinee is not daunted in the serial arrangement of the X-ray CT imaging apparatus and the PET imaging apparatus. Further, it is possible to provide a highly quantitative image with a high resolution and achieve examinations with high accuracy.

Embodiment 2

Figure 19A:
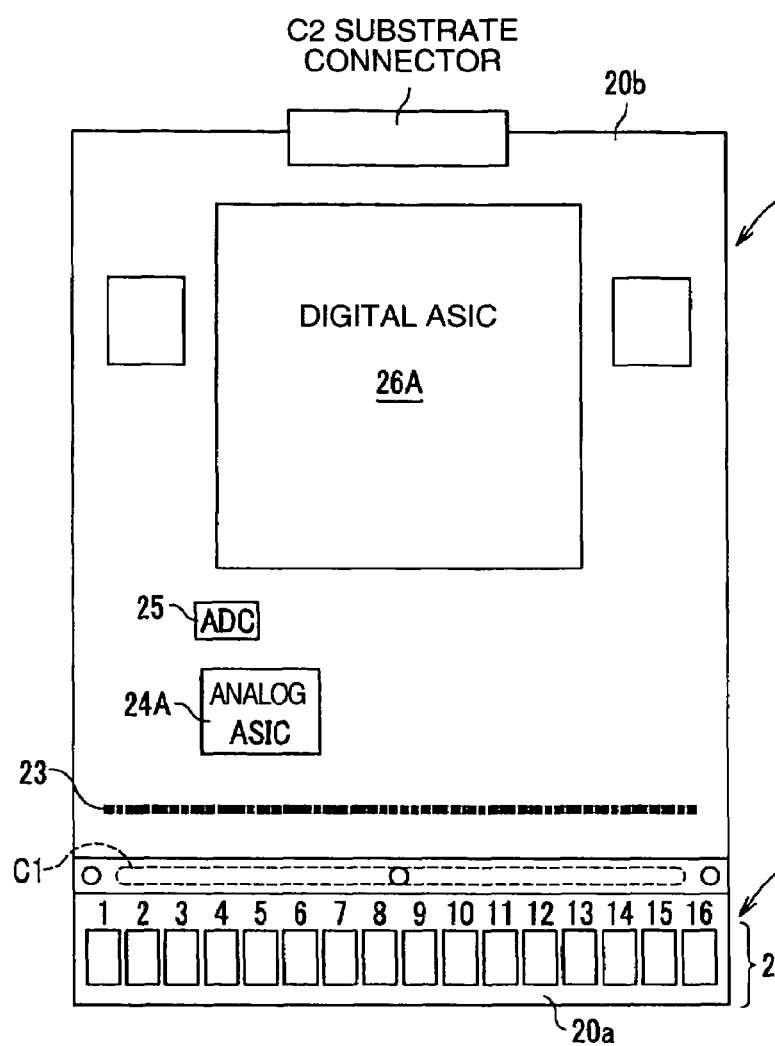
FIG. 19A is a front view showing a combined substrate in which a detector substrate and an ASIC substrate of the semiconductor radiation detector of the present embodiment are combined.
Figure 19B:
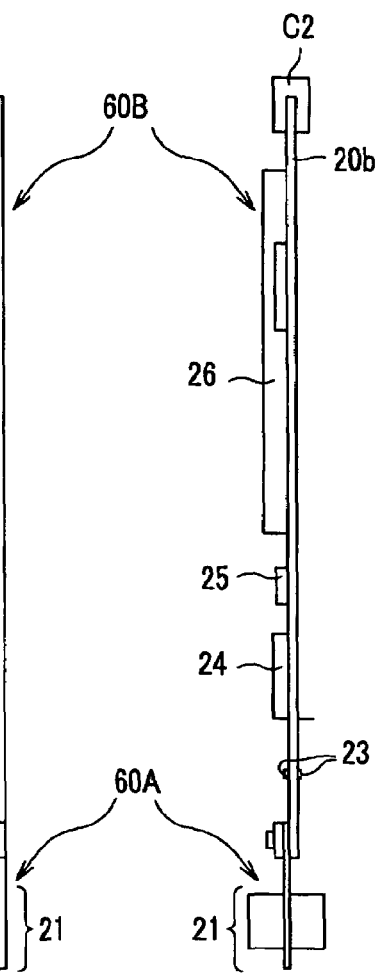
FIG. 19B is a side view of FIG. 19A.

A radiological imaging system of another embodiment will be described below. As shown in FIG. 18, the present embodiment is different from Embodiment 1 in that semiconductor radiation detectors 21 are used as a radiation detector in an X-ray CT imaging apparatus 4. To be specific, a plurality of combined substrates 60 shown in FIGS. 19A, 19B are provided in a slicing direction (four slices in the present embodiment) via a detector holding part 46, and the combined substrates 60 rotates around an examinee H in synchronization with an X-ray source circumferential moving apparatus 41. As with the combined substrate 20 of Embodiment 1, the combined substrate 60 has detectors 21, resistors 23, analog ASICs 24A, ADCs 25, and a digital ASIC 26A. This configuration is similar to that of Embodiment 1 except for a smaller number of detectors 21, the analog ASIC 24, and the ADC 25. That is, 16 detectors 21 are provided in one line and thus 32 detectors 21 are provided on both sides. one analog ASIC 24 and one ADC 25 are provided accordingly.

Imaging in the X-ray CT imaging apparatus 4 having such detectors 21 is performed by moving the bed 14 to move the examinee H between the X-ray source 45 and the detectors 21. At this point, the X-ray source 45 and the detectors 21 rotate around the examinee H by rotating the disk-like holding part 44. Then, X-rays radiated from the X-ray source 45 are incident on the corresponding detectors 21 while spreading to a desired degree. The detectors 21 output X-ray detection signals. The X-ray detection signals are processed by the analog ASIC 24A and the digital ASIC 26 which will be discussed later.

Referring to FIGS. 20 and 21, an ASIC substrate 60B constituting the combined substrate (unit substrate) 60 will be described below. An ASIC substrate 60B connected to a detector substrate 60A via a connector C1 has the resistor 23 provided for each of the detectors 21, one analog ASIC 24A, and one digital ASIC 26A. The analog ASIC 24A has 32 sets of analog signal processing circuits (analog signal processors) 33A. The analog signal processing circuits 33A is provided for each of the detectors 21. In this configuration, a charge amplifier 24b, a polarity amplifier 24c, a band pass filter 24d, and a peak hold circuit 24e are connected in this order. One analog ASIC 24A is an LSI which integrates the 32 sets of analog signal processing circuits 33A. An X-ray detection signal having outputted from the detector 21 and passed through the resistor 23 is inputted to the peak hold circuit 24e via the charge amplifier 24b, the polarity amplifier 24c, and the band pass filter 24d. The peak hold circuit 24e samples and holds the intensity of the X-ray detection signal.

The digital ASIC 26A has a packet data generation apparatus 34 and a data transfer circuit 37, which are integrated into an LSI. The digital ASIC 26A receives a 64 MHz clock signal from a clock generating apparatus (crystal oscillator, not shown) and operates synchronously. A driving start signal outputted from a drive controller 42 is received by an ADC control circuit 36 via a unit combination LSI 31 and measurement is started. The ADC control circuit 36 has a counter therein to manage measurement time. That is, the ADC 25 is operated at predetermined time intervals and peak value information is read while channels are switched. At the same time, the analog ASIC 24A is controlled to switch peak value output channels and reset the charge amplifier. The ADC control circuit 36 generates packet data which is digital information including time information, detector IDs, and peak value information. The packet data outputted from the ADC control circuits 36 is periodically transmitted from a data transfer circuit 37 to the unit combination FPGA 31 of a detector unit 2A. The unit combination FPGA 31 outputs the packet data, which has been inputted from the data transfer circuit 37 of each of the combined substrates 60, at a time to information transmission wiring connected to a connector 38.

The packet data outputted from the unit combination FPGA 31 is sent to a data processing apparatus 12A. By using detector ID information and time information, the data processing apparatus 12A determines the position coordinates of the detector 21 corresponding to the detector ID information when X-rays are detected. The position coordinates indicate the position of the detector 21 when the X-rays are detected, the detector 21 revolving on the revolving orbit of a disk-like holding part 44. Since the revolving disk-like holding part 44 has a constant angular speed, the position (position coordinates) of the detector 21 at the detection of X-rays can be determined by using time determined by a time decision circuit 35. The data processing apparatus 12A generates tomographic information of an examinee H based on the X-ray CT data detected on the position of the detector 21 that is determined by the packet data. The tomographic information is displayed on a display apparatus 13. The packet information, the position information of the detector 21, and the tomographic information are stored in the storage apparatus of the data processing apparatus 12A.

In addition to the effects (1) to (6), the present embodiment has the following effect:

(7) In the present embodiment, the semiconductor radiation detector is used as a detector of the X-ray CT imaging apparatus, the ASIC, etc. is used as a signal processing circuit, and these elements are orderly arranged on the combined substrate, so that the X-ray CT imaging apparatus is miniaturized. Therefore, it is possible to miniaturize the overall apparatus so that an examinee is not daunted in the serial arrangement of the X-ray CT imaging apparatus and the PET imaging apparatus.

In the foregoing embodiments, a member used for mounting (housing) the detector unit 2 in the PET imaging apparatus 1 and the X-ray CT imaging apparatus 4 is not limited to the unit support member 2A. Any mounting/housing means or method can be used.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A radiological imaging system, comprising:
a bed for carrying an examinee,
a positron emission CT imaging apparatus and an X-ray CT imaging apparatus disposed along a longitudinal direction of said bed,
wherein said positron emission CT imaging apparatus includes a plurality of unit substrates including a plurality of semiconductor radiation detectors for detecting a γ-ray emitted from said examinee and an integrated circuit for processing γ-ray detection signals outputted from each of said plurality of semiconductor radiation detectors, said unit substrates being arranged in a direction perpendicular to said longitudinal direction of said bed and around said bed,
wherein said semiconductor radiation detectors are disposed on both sides of each of said unit substrates,
wherein each of said semiconductor radiation detectors has a laminated structure comprising at least two layers, each layer including a layer of semiconductor material sandwiched with anode and cathode electrodes,
said X-ray CT imaging apparatus has an X-ray source for emitting an X-ray to said examinee and a radiation detector for detecting an X-ray emitted from said X-ray source and passed through said examinee, and
said bed is shared by said positron emission CT imaging apparatus and said X-ray CT imaging apparatus.

2. The radiological imaging system according to claim 1, wherein said integrated circuit comprises an analog integrated circuit for processing signals output from said semiconductor radiation detectors, an AD converter for converting an analog signal output from said analog integrated circuit into a digital signal, and a digital integrated circuit for processing said digital signal output from said AD converter,
wherein said analog integrated circuit comprises a plurality of signal processing apparatuses each being provided for each of said semiconductor radiation detectors,
wherein said digital integrated circuit comprises an ADC controller for outputting a control signal to said AD converter, said control signal including information for identifying said semiconductor radiation detectors on the basis of signals from said signal processing apparatuses,
wherein one said AD converter is provided for said plurality of signal processing apparatuses, and by said one AD converter, an analog signal output from a signal processing apparatus corresponding to a control signal input from said ADC controller is converted into a digital signal and output said digital signal to said digital integrated circuit.

3. The radiological imaging system according to claim 1, further comprising a housing member for housing said unit substrates, said housing member having light shielding properties,
wherein another integrated circuit is attached on an outer surface of said housing member, said another integrated circuit being proved for outputting information output from said integrated circuit included in said unit substrates to an external device.

4. The radiological imaging system according to claim 3, said another integrated circuit is a combination integrated circuit capable of programming a program for processing information output from said integrated circuits of each of said unit substrates in a combined manner.

5. The radiological imaging system according to claim 1, wherein said radiation detectors of said X-ray CT imaging apparatus are semiconductor radiation detectors.

6. The radiological imaging system according to claim 5, wherein a plurality of said semiconductor radiation detectors are arranged in a longitudinal direction of said bed.

7. The radiological imaging system according to claim 1, further comprising a tomographic information creation apparatus for creating tomographic information by using second information obtained based on first information output from said integrated circuit.

8. The radiological imaging system according to claim 7, wherein said integrated circuit comprises an analog integrated circuit for processing signals output from said semiconductor radiation detectors, an AD converter for converting an analog signal output from said analog integrated circuit into a digital signal,
and a digital integrated circuit for processing said digital signal output from said AD converter.

9. The radiological imaging system according to claim 8, wherein said semiconductor radiation detectors, said analog integrated circuit, said AD converter and said digital integrated circuit are arranged in this order from one end of said unit substrate to the other end in a longitudinal direction of said unit substrate.

10. The radiological imaging system according to claim 8, wherein said analog integrated circuit has a function for amplifying a signal, and said digital integrated circuit has a function for generating time information.

11. The radiological imaging system according to claim 8, wherein said analog integrated circuit comprises a plurality of signal processing apparatuses which are provided respectively for each of said semiconductor radiation detectors, each of said signal processing apparatuses including an amplifier to process a radiation detection signal output from said semiconductor radiation detectors, said digital integrated circuit outputs time information indicative of a detection time of γ-ray and identification information identifying said semiconductor radiation detectors based on an output of said signal processing apparatuses, and said radiological imaging system further comprises a coincidence detection apparatus for conducting coincidence detection based on said time information, and said tomographic information creation apparatus for creating said tomographic information by using said identification information and information obtained by said coincidence detection apparatus.

12. The radiological imaging system according to claim 8, wherein said analog integrated circuit has a slow system which includes an amplifier and a peak value output apparatus for receiving an output of said amplifier and outputting a peak value of a radiation detection signal, and a fast system which includes a timing detection apparatus for receiving said radiation detection signal from upstream of said amplifier and outputting a radiation detection timing signal, said digital integrated circuit includes a time information creation apparatus which is provided for each of said semiconductor radiation detectors and creates time information indicative of a detection time of γ-ray based on said radiation detection signal, and said radiological imaging system further comprises a coincidence detection apparatus for conducting coincidence detection based on said time information, and said tomographic information creation apparatus for creating said tomographic information by using identification information identifying said semiconductor radiation detectors and information obtained by said coincidence detection apparatus.

13. The radiological imaging system according to claim 12, wherein said digital integrated circuit further comprises an AD conversion control apparatus which identifies, when time information is input from said time information creation apparatus, one of position information and said identification information of said semiconductor radiation detectors connected to said time information creation apparatus and an information combination apparatus which combines said one of said position information and said identification information, said time information, and peak value information, and said AD converter converts, to peak value information which is digital information, a peak value which is output from said peak value output apparatus determined by said information identified by said AD conversion control apparatus out of a plurality of peak value output apparatuses of a plurality of signal processing apparatuses included in said analog integrated circuit, and said AD converter outputs converted information to said information combination apparatus.

14. The radiological imaging system according to claim 1, wherein said unit substrate includes a first substrate and a second substrate, said first substrate has at least said semiconductor radiation detectors, and said second substrate has at least said integrated circuit.

15. The radiological imaging system according to claim 14, wherein said first substrate and said second substrate are joined to each other in a detachable/attachable manner.

16. The radiological imaging system according to claim 15, wherein said first substrate and said second substrate are lapped over at the end of said substrates.

17. The radiological imaging system according to claim 1, wherein said positron emission CT imaging apparatus is a 3D-specific positron emission CT imaging apparatus having no septa for 2D imaging or radiation source for adsorption correction.

18. The radiological imaging system according to claim 1, wherein each of said semiconductor radiation detectors has a semiconductor region for interacting with a radiation to generate charge, an anode electrode and a cathode electrode are opposed to each other via said semiconductor region, a distance between said anode electrode and said cathode electrode or a thickness of said semiconductor region between said anode electrode and said cathode electrode is 0.2 to 2 mm.

19. The radiological imaging system according to claim 18, wherein a distance between said electrodes or a thickness of said semiconductor region is 0.5 to 1.5 mm.

20. The radiological imaging system according to claim 1, wherein said positron emission CT imaging apparatus comprises a support member and a plurality of detector units attached to said support member in a detachable/attachable manner, and each of said detector units comprises a housing member and a plurality of unit substrates which are housed in said housing member in a detachable/attachable manner.

21. The radiological imaging system according to claim 20, wherein said housing member comprises a plurality of guide members for guiding said unit substrates into said housing member.

22. The radiological imaging system according to claim 20, wherein each of said detector units comprises a voltage boosting apparatus for boosting a voltage and wiring for supplying a voltage from said voltage boosting apparatus to each of said semiconductor radiation detectors of said unit substrates.

23. The radiological imaging system according to claim 20, wherein said housing member has light shielding properties.

24. The radiological imaging system according to claim 1, wherein each of said unit substrates comprises said plurality of semiconductor radiation detectors arranged in a form of lattice at a portion near said bed and said integrated circuit arranged at a farther portion from said bed.

\* \* \* \* \*